(12) United States Patent
Arioli et al.

(10) Patent No.: US 9,371,564 B2
(45) Date of Patent: Jun. 21, 2016

(54) METHODS FOR PLANT FIBER CHARACTERIZATION AND IDENTIFICATION

(75) Inventors: Antonio Arioli, Ashwood (AU); Steven Engelen, Lokeren (BE)

(73) Assignee: Bayer Bioscience N.V., Ghent (BE)

( * ) Notice: Subject to any disclaimer, the term of this patent is extended or adjusted under 35 U.S.C. 154(b) by 1127 days.

(21) Appl. No.: 13/056,192

(22) PCT Filed: Aug. 6, 2009

(86) PCT No.: PCT/EP2009/005891
§ 371 (c)(1),
(2), (4) Date: Aug. 10, 2011

(87) PCT Pub. No.: WO2010/015423
PCT Pub. Date: Feb. 11, 2010

(65) Prior Publication Data
US 2011/0289022 A1 Nov. 24, 2011

Related U.S. Application Data

(60) Provisional application No. 61/188,613, filed on Aug. 11, 2008.

(30) Foreign Application Priority Data

Aug. 8, 2008 (EP) .................................. 08014211

(51) Int. Cl.
*C12Q 1/68* (2006.01)
*G01N 33/53* (2006.01)
*C12N 15/00* (2006.01)
*G06Q 99/00* (2006.01)

(52) U.S. Cl.
CPC .............. *C12Q 1/6881* (2013.01); *G06Q 99/00* (2013.01); *C12Q 2600/158* (2013.01)

(58) Field of Classification Search
CPC ........ C12Q 1/68; C12Q 1/6876; G01N 33/53; C12N 15/00
USPC ........................... 435/6.1, 7.1; 536/22.1, 25.4
See application file for complete search history.

(56) References Cited

U.S. PATENT DOCUMENTS

| | | | |
|---|---|---|---|
| 4,761,373 A | 8/1988 | Anderson et al. | |
| 5,013,659 A | 5/1991 | Bedbrook et al. | |
| 5,141,870 A | 8/1992 | Bedbrook et al. | |
| 5,273,894 A | 12/1993 | Strauch et al. | |
| 5,276,268 A | 1/1994 | Strauch et al. | |
| 5,304,732 A | 4/1994 | Anderson et al. | |
| 5,331,107 A | 7/1994 | Anderson et al. | |
| 5,361,450 A * | 11/1994 | Shofner et al. ............... 19/66 R |
| 5,378,824 A | 1/1995 | Bedbrook et al. | |
| 5,463,175 A | 10/1995 | Barry et al. | |
| 5,561,236 A | 10/1996 | Leemans et al. | |
| 5,605,011 A | 2/1997 | Bedbrook et al. | |
| 5,637,489 A | 6/1997 | Strauch et al. | |
| 5,646,024 A | 7/1997 | Leemans et al. | |
| 5,648,477 A | 7/1997 | Leemans et al. | |
| 5,731,180 A | 3/1998 | Dietrich | |
| 5,739,082 A | 4/1998 | Donn | |
| 5,767,361 A | 6/1998 | Dietrich | |
| 5,776,760 A | 7/1998 | Barry et al. | |
| 5,908,810 A | 6/1999 | Donn | |
| 5,928,937 A | 7/1999 | Kakefuda et al. | |
| 7,112,665 B1 | 9/2006 | Leemans et al. | |
| 8,669,079 B2 * | 3/2014 | Liang et al. ................. 435/91.2 |
| 2004/0123342 A1 * | 6/2004 | Elliott et al. ................. 800/278 |
| 2005/0112610 A1 * | 5/2005 | Lee et al. ........................ 435/6 |
| 2006/0105167 A1 * | 5/2006 | Ogawa ..................... B32B 5/00 428/355 AK |
| 2006/0110756 A1 * | 5/2006 | Tang et al. ........................ 435/6 |
| 2008/0242175 A1 * | 10/2008 | Narayanan et al. ........... 442/136 |
| 2010/0167040 A1 * | 7/2010 | Ruan et al. ................ 428/292.1 |
| 2011/0250594 A1 * | 10/2011 | Liang et al. ................. 435/6.11 |
| 2011/0289022 A1 * | 11/2011 | Arioli et al. .................. 705/500 |

FOREIGN PATENT DOCUMENTS

| | | |
|---|---|---|
| EP | PCT/EP05/010168 | 9/2005 |
| EP | 0837944 | 3/2006 |
| EP | PCT/EP2007/004142 | 5/2007 |
| WO | 9421795 | 9/1994 |
| WO | 9633270 | 10/1996 |
| WO | 9638567 | 12/1996 |
| WO | 9800549 | 1/1998 |
| WO | 9924585 | 5/1999 |
| WO | 9924586 | 5/1999 |
| WO | 9934008 | 7/1999 |
| WO | 0004173 | 1/2000 |
| WO | 0066746 | 11/2000 |
| WO | 0066747 | 11/2000 |
| WO | 0117333 | 3/2001 |

(Continued)

OTHER PUBLICATIONS

Akin et al.., Enzyme-retting of flax and characterization of processed fibers. Journal of Biotechnology 89 :193 (2001).*
Barker et al., Two Methods of Whole-Genome Amplification enable Accurate Genotyping Across a 2320-SNP Linkage Panel. Genome Research 14 : 901 (2004).*
Marota et al., DNA Decay Rate in Papyri and Human Remains From Egyptian Archaeological Sites. Journal of Physical Anthropology 117 :310 (2002).*
Paterson et al., A Rapid Method for Extraction of Cotton (*Gossypium* spp.) Genomic DNA Suitable for RFLP or PCR Analysis . . . Plant Molecular Biology Reporter. 11 (2) : 122 (1993).*
Auer, C. Tracking genes from seed to supermarket: techniques and trends. Trends in Plant Science 8 (12) : 591 (2003).*

(Continued)

*Primary Examiner* — Ethan Whisenant

(57) ABSTRACT

Methods are provided for the isolation of biological macromolecules including peptides, proteins, and nucleic acids from mature plant fibers such as cotton fibers and from textiles. The biological macromolecules can be used to characterize the plant fiber (source, origin, genomic composition of producing plant etc.).

19 Claims, 8 Drawing Sheets

(56) References Cited

FOREIGN PATENT DOCUMENTS

| | | |
|---|---|---|
| WO | 0124615 | 4/2001 |
| WO | 0166704 | 9/2001 |
| WO | 0226995 | 4/2002 |
| WO | 0236782 | 5/2002 |
| WO | 0236787 | 5/2002 |
| WO | 0245485 | 6/2002 |
| WO | 03013226 | 2/2003 |
| WO | 03092360 | 11/2003 |
| WO | 2004024928 | 3/2004 |
| WO | 2004040012 | 5/2004 |
| WO | 2004065557 | 8/2004 |
| WO | 2004090140 | 10/2004 |
| WO | 2004106529 | 12/2004 |
| WO | 2005012515 | 2/2005 |
| WO | 2005017157 | 2/2005 |
| WO | 2005020673 | 3/2005 |
| WO | 2005093093 | 10/2005 |
| WO | 2006007373 | 1/2006 |
| WO | 2006015376 | 2/2006 |
| WO | 2006024351 | 3/2006 |
| WO | 2006060634 | 6/2006 |
| WO | 2006133827 | 12/2006 |
| WO | 2006136351 | 12/2006 |
| WO | 2007017186 | 2/2007 |
| WO | 2007024782 | 3/2007 |
| WO | 2007027777 | 3/2007 |
| WO | 2007107326 | 9/2007 |
| WO | 2008012058 | 1/2008 |

OTHER PUBLICATIONS

Bayley et al., Engineering 2,4-D resistance into cotton. Theoretical and Applied Genetics 83 : 645 (1992).*

Chen et al.,Toward Sequencing Cotton (*Gossypium*) Genomes. Plant Physiology 145 : 1303 (2007).*

Dellaporta et al. A Plant DNA Minipreparation : Version II Plant Molecular Biology Reporter 1 (4) : 19 (1983).*

Dellaporta et al. Plant DNA Miniprep and Microprep : Versions 2.1 -2.3 Ch. 84 of the Maize Handbook (1994).*

Firoozabady et al., Transformation of cotton (*Gossypium hirsutum* L.) by Agrobacterium tumefaciens and regeneration of transgenic plants. Plant Molecular Biology 10 : 105 (1987).*

He et al.,QTL mapping for economic traits based on a dense genetic map of cotton with PCR-based markers using the interspecific cross of *Gossypium hirsutum* X *Gossypium barbadense*. Euphytica 153 : 181 (2007—published online on Sep. 1, 2006).*

John, M. .An efficient method for isolation of RNA and DNA from plants containing polyphenolics. Nucleic Acids Research 20 (9) : 2381 (1992).*

Mirahlia et al., Detection and traceability of genetically modified organisms in the food production chain. Food and Chemical Toxicology 42 : 1157 (2004).*

Yang et al., Validation of a cotton-specific gene, Sad1, used as an endogenous reference gene in qualitative and real-time quantitative PCR detection of transgenic cottons. Plant Cell Reports 24 : 237 (2005).*

Yang et al., Qualitative and quantitative PCR methods for event-specific detection of genetically modified cotton Mon1445 and Mon531 Transgenic Research 14 : 817 (2005).*

Nida et al., Glyphosate-Tolerant Cotton: Genetic Characterization and Protein Expression. J. Agric. Food Chem. 1996, 44, 1960-1966.*

Reinisch et al. A Detailed RFLP Map of Cotton, *Gossypium hirsutum* X *Gossypium barbadense*: Chromosome Organization and Evolution in a Disomic Polyploid Genome. Genetics 138 : 829 (1994).*

Gill et al. Forensic application of DNA 'fingerprints'. Nature 318 :577 (1985).*

Yang, Litao et al., "Identification and Quantification of Three Genetically Modified Insect Resistant Cotton Lines Using Conventional and TaqMan Real-Time Polymerase Chain Reaction Methods", Journal of Agric. Food Chem., vol. 53, p. 6222-6229, 2005.

Crickmore, N. et al., "Revision of the Nomenclature for the Bacillus thuringiensis Pesticidal Crystal Proteins", Microbiology and Molecular Biology Reviews, vol. 62, No. 3, p. 807-813, Sep. 1998.

Crickmore et al., "Bacillus thuringiensis Toxin Nomenclature", online at http://www.lifesci.sussex.ac.uk/Home/Neil.Crickmore/Bt/.

Cronn, Richard C. et al., "Rapid Diversification of the Cotton Genus (*Gossypium*: Malvaceae) Revealed by Analysis of Sixteen Nuclear and Chloroplast Genes", American Journal of Botany, vol. 89, No. 4, p. 707-725, 2002.

Gasser, Charles S. et al., "Structure, Expression, and Evolution of the 5-Enolpyruvylshikimate-3-Phosphate Synthase Genes of Petunia and Tomato", Journal of Biological Chemistry, vol. 263, No. 9, p. 4280-4289, 1988.

Giardina, Emiliano et al., "Whole Genome Amplification and Real-Time PCR in Forensic Casework", BMC Genomics, vol. 10, No. 159, 2009.

Graves, D.A. et al., "Chronology of the differentiation of cotton (*Gossypium hirsutum* L.) fiber cells", Planta, vol. 15, p. 254-258, 1988.

Hayashi, Takahisa et al., "Xyloglucan in the cell walls of cotton fiber", Carbohydrate Research, vol. 181, p. 273-277, 1988.

Hsu, Chuan-Yu et al., "Transcriptional regulation of the lipid transfer protein gene LTP3 in cotton fibers by a novel MYB protein", Plant Science, vol. 168, p. 167-181, 2005.

Huwyler, H.R. et al., "Changes in the Composition of Cotton Fibre Cell Walls during Development", Planta, vol. 146, p. 635-642, 1979.

Iqbal, Saima et al., "Identification of differentially expressed genes in developing cotton fibers (*Gossypium hirsutum* L.) through differential display", Electronic Journal of Biotechnology, vol. 11, No. 4, 2008.

Kim, Hee Jin et al., "Cotton Fiber Growth in Planta and in Vitro. Models for Plant Cell Elongation and Cell Wall Biogenesis", Plant Physiology, vol. 127, p. 1361-1366, 2001.

Lee, Seong-Hun et al., "Detection Methods for Biotech Cotton MON 15985 and MON 88913 by PCR", Journal of Agric. Food Chem., vol. 55, p. 3351-3357, 2007.

Luo, Ming et al., "Cloning and Expression Analysis of a Brassinosteroid Biosynthetic Enzyme Gene, GhDWF1, from Cotton (*Gossypium hirsuturm* L.)", Agricultural Sciences in China, vol. 6, No. 11, p. 1297-1305, 2007.

Meinert, Maureen C., "Changes in Biochemical Composition of the Cell Wall of the Cotton Fiber During Development", Plant Physiol., vol. 59, p. 1088-1097, 1977.

Moellenbeck, Daniel J., "Insecticidal proteins from Bacillus thuringiensis protect corn from corn rootworms", Nature Biotechnology, vol. 19, p. 668-672, 2001.

Peng, Liangcai et al., "Sitosterol-β-glucoside as Primer for Cellulose Synthesis in Plants", Science, vol. 295, p. 147-150, 2002.

Pfluger, Jennifer et al., "Cell growth: The power of symplastic isolation", Current Biology, vol. 11, p. R436-R439, 2001.

Ruan, Yong-Ling et al., "A Fiberless Seed Mutation in Cotton is Associated with Lack of Fiber Cell Initiation in Ovule Epidermis and Alterations in Sucrose Synthase Expression and Carbon Partitioning in Developing Seeds", Plant Physiol, vol. 118, p. 399-406, 1998.

Ruan, Yong-Ling et al., "Pathway and control of sucrose import into initiating cotton fibre cells", Aust. J. Plant Physiol, vol. 27, p. 795-800, 2000.

Ruan, Yong-Ling et al., "The Control of Single-Celled Cotton Fiber Elongation by Developmentally Reversible Gating of Plasmodesmata and Coordinated Expression of Sucrose and K+ Transporters and Expansin", The Plant Cell, vol. 13, p. 47-60, 2001.

Schnepf, H. Ernest et al., "Characterization of Cry34/Cry35 Binary Insecticidal Proteins from Diverse Bacillus thuringiensis Strain Collections", Applied and Environmental Microbiology, vol. 71, No. 4, p. 1765-1774, 2005.

Van't Hof, Jack, "Increased Nuclear DNA Content in Developing Cotton Fiber Cells", American Journal of Botany, vol. 86, No. 6, p. 776-779, 1999.

(56) References Cited

OTHER PUBLICATIONS

Z. Yuan, et al., The application of DNA analysis technology in identification of animal fibers, China Fiber Inspection, 4 (2006). (English translation attached).

P. Gao, et al., Identification of genes preferentially expressed in cotton fibers: A possible role of calcium signaling in cotton fiber elongation, Plant Science 173 (2007) 61-69.

* cited by examiner

METHODS FOR PLANT FIBER CHARACTERIZATION AND IDENTIFICATION

CROSS-REFERENCE TO RELATED APPLICATIONS

This application is a §371 U.S. National Stage of International Application No. PCT/EP2009/005891, filed Aug. 6, 2009, which claims the benefit of U.S. Patent Application Ser. No. 61/188,613, filed Aug. 11, 2008, and European Patent Application No. 08014211.0, filed Aug. 8, 2008, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS082011PCTUS01SequenceListing.txt", created on Jan. 26, 2011, and having a size of 5,000 bytes and is filed concurrently with the specification. The sequence listing contained in this ASCII formatted document is part of the specification and is herein incorporated by reference in its entirety.

FIELD OF THE INVENTION

The current invention relates to methods for isolating biological macromolecules including peptides, proteins, and nucleic acids from mature plant fibers such as cotton fibers. The plant fibers may have been processed into yarns, which in turn may be woven or knitted to fabric or finished apparel, prior to the isolation of the biological macromolecules. Since the isolated macromolecules contain information encoded in the sequence of their building blocks, these macromolecules isolated from plant fibers according to the currently described methods may be conveniently used to characterize the plant fiber or identify the origin or source of the plant fiber. The resulting information may be used e.g. in identity preservation programs for special plant fibers, certification of origin of plant fibers or even in reconstruction of breeding pedigrees using historical sources of plant fibers.

BACKGROUND OF THE INVENTION

Plant fibers form a source for economically important products such as paper, cordage (cords and ropes) and textiles. A fiber is botanically defined as a long narrow tapering cell, dead and hollow at maturity with a rigid thick cell wall composed mostly of cellulose and usually lignin. Soft or bast fibers are found in the phloem (inner bark) of dicotyledonous stems (flax, jute, hemp, ramie). Hard or leaf fibers are found in monocot leaf vascular bundles (sisal, manilla hemp, pineapple). Surface fibers grown from the surface of seeds (cotton), leaves or fruits (coconut coir).

Cotton provides much of the high quality fiber for the textile industry and major efforts have been invested in obtaining cotton fibers with characteristics which suit the requirements of the industry through breeding by either classical methods or by genetically altering the genome of cotton plants.

Cotton fiber originates as a seed trichome, more specifically a single cell that initiates from the epidermis of the outer integument of the ovules, at or just prior to anthesis. The morphological development of cotton fibers has been well documented (Basra and Malik, 1984, Int Rev of Cytology 89: 65-113; Graves and Stewart, 1988, supra; Ramsey and Berlin, 1976, American Journal of Botany 63 (6): 868-876; Ruan and Chourey, 1998, Plant Physiology 118: 399-406; Ruan et al. 2000, Aust. J. Plant Physiol. 27:795-800; Stewart, 1975, Am. J. Bot. 62, 723-730). Cotton fibers, in particular from *Gossypium hirsutum*, undergo four overlapping developmental stages: fiber cell initiation, elongation, secondary cell wall biosynthesis, and maturation. Fiber cell initiation is a rapid process. White fuzzy fibers begin to develop immediately after anthesis and continue up to about 3 days post-anthesis (DPA), which is followed by fiber cell elongation (until about 10 to about 17 DPA). Depending upon growth conditions, secondary cell wall biosynthesis initiates and continues to about 25 to about 40 DPA, followed by a maturation process until about 45 to about 60 DPA. The secondary cell wall synthesis and maturation phase are commonly considered the "fiber strength building phase". Only about 25 to 30% of the epidermal cells differentiate into the commercially important lint fibers (Kim and Triplett, 2001). The majority of cells does not differentiate into fibers or develop into short fibers or fuzz. During fiber elongation and secondary wall metabolism, the fiber cells elongate rapidly, synthesize secondary wall components, and show dramatic cellular, molecular and physiological changes. Fiber elongation is coupled with rapid cell growth and expansion (Seagull, 1991. In *Biosynthesis and biodegradation of cellulose* (Haigler, C. H. & Weimer, P. J., eds) pp. 1432163, MarcelDekker, New York) and constant synthesis of a large amount of cell metabolites and cell wall components such as cellulose. About 95% of the dry-weight in mature cotton fibers is cellulose (Pfluger and Zambryski, 2001, Curr Biol 11: R436-R439; Ruan et al., 2001, Plant Cell 13: 47-63). Non-celluloid components are also important to fiber cell development (Hayashi and Delmer, 1988, Carbohydr. Res. 181: 273-277; Huwyler et al., 1979, Planta 146: 635-642; Meinert and Delmer, 1977, Plant Physiol 59: 1088-1097; Peng et al., 2002, Science 295: 147-150). Compared to other plant cells, cotton fibers do not contain lignin in secondary walls but have large vacuoles that are presumably related to rapid cell growth and expansion (Basra and Malik, 1984, supra; Kim and Triplett, 2001, Plant Physiology 127: 1361-1366; Mauney, 1984, supra; Ruan and Chourey, 1998, supra; Ruan et al., 2000, supra; Van't Hof, 1999, American Journal of Botany 86: 776-779).

Developing cotton fiber cells are living cells and accordingly contain biological macromolecules such as peptides, proteins, and nucleic acids such as DNA and RNA. In contrast, mature fibers are dead, hollow cells, consisting mainly of cellulose. It is generally accepted that fiber cells, particularly cotton fiber cells, no longer contain extractable nucleic acids or proteins. Based on this inertness, cotton swabs are used as an applicator for medical substances as well as to take DNA samples from, most commonly, the inner cheek in forensic investigations.

In addition, plant fibers are subject to extensive processing prior to their use in industry, particularly prior to their use in the textile industry. In the case of cotton, processing from raw fiber in the field to finished apparel for sale involves numerous steps that vary greatly depending on the end product desired. The various possible steps in these processes can be divided generally into mechanical and chemical steps.

The process of harvesting and ginning cotton can subject the fiber to thermal and mechanical damage. No chemicals are applied during the ginning process. Heat is often utilized to dry cotton during the ginning process if it contains more than 8% moisture. Heat is usually closely regulated to avoid fiber damage. Mechanical damage can occur during the picking and ginning operations. This mechanical damage should affect a very low % of the total fibers.

During spinning, the process steps are primarily mechanical. Short fibers (immature and/or mechanically damaged fibers and foreign material are removed in the spinning process). The first chemical treatments in processing are made toward the end of the spinning process when yarn for knitting is treated with a lubricant and about half the yarn for weaving is treated with sizing material. Cotton yarn for knitting is most often treated with wax as a lubricant to facilitate movement of the yarn through the knitting equipment. Synthetic lubricants are also available but it is believed wax is still the most common treatment. Sizing, also called slashing, is applied to the yarn for weaving that will be used as the lengthwise strands in the finished fabric (the warp). The lateral (fill) yarn is not treated with sizing. The common material used for sizing is starch. Polyvinyl alcohol is also used for sizing and blends of starch and polyvinyl alcohol are common. Additives such as binders, humectants, softeners, wetting agents, defoamers and other adjuvants may be added to the sizing treatment.

Knitting and weaving are both mechanical processes involving no chemical or heat applications. At the end of the knitting and weaving processes, steps to prepare the resulting fabric for finishing involve the application of chemicals and in some cases, high temperatures. The preparation process objective of the finishing step is to remove impurities that will interfere with processing through dyeing, printing or other finishing steps. Primarily, the wax must be removed from knitted fabric (scouring) and the sizing must be removed from woven fabric (desizing). Other impurities that may be removed at this step include, seed husks, pectins and other chemicals. Chemicals used for desizing include enzymes to remove starch and soda, ash or detergents to remove polyvinyl alcohol. Scouring is done with organic solvents that will dissolve the wax or other lubricants used. After scouring or desizing, fabric is usually bleached using chlorine or peroxide bleach. Goals of bleaching are to remove any remaining non-fibrous material, hydrolysis, oxidation and removal of residual sizeing and improve absorbancy of dye. Bleaching with peroxide may involve steam or water bath at near boiling water temperatures and the bleach bath may contain additives such as stabilizers and sequestering agents. Bleaching with chlorine is done at lower temperatures (40 to 50 degrees Centegrade) and cellulose degradation is less than with peroxide. If chlorine is used for bleaching, an antichlor treatment is also required. Singeing with a controlled flame is carried out on some fabrics to clean the fabric surface and remove or reduce pilling. Optical brighteners may be added to fabrics or garments to be sold as white un-dyed products. Anionic organic optical brighteners are typically used on cotton. Several compounds are available and some can be added during bleaching.

Mercerization is a process that can be applied to cotton yarn or fabric to improve absorption of or reaction to dye and other chemical finishing treatments, improve breaking strength, improve dimensional stability, improve fabric smoothness and luster and cover immature cotton fibers. It is a process that involves treatment with NaOH, washing, acid scouring, rinsing and drying.

The most common finishing treatment is dyeing. It can be done at the yarn, fabric or garment stage. Dyes used for cotton are numerous and of many different types. The most common dye product for cotton is indigo but it represents only 4% of dyed fabric. Dyeing can be done as a continuous process or batch process. While the chemicals used for dyeing are numerous, the process customarily involves the use of high temperature, near boiling, in the dye vat to which the fabric, yarn or garments may be submersed for extended time. Printing is the other major process for adding color or design to textiles. Printing involves mostly a mechanical process for applying coloring inks to the surface of fabric or garments. Both dyeing and printing may involve the application of chemical fixing agents at the end of the process.

Another common finishing treatment, especially after dyeing is aggressive laundering. This would include use of detergents and other cleaning agents to remove residual finishing materials from the finished fabric or garment.

Many other mechanical and chemical finishing steps may be applied to fabric, yarn or garments involving numerous options of chemicals and treatment processes. Softeners alone may be of three different types and each type may involve several different chemicals.

Although the above overview of converting raw cotton fiber into end use textile products is highly generalized, it will be clear that a person skilled in the art would not expect to be able to extract peptides, proteins or nucleic acids from yarns, textiles or finished apparel products after the numerous chemical and thermal treatment steps customarily involved.

There is a need in the industry to be able to track the source and/or origin of plant fibers, particularly of mature and/or processed plant fibers. Such source and/or origin identification of plant fibers may be important for certification processes, guaranteeing production and processing of fibers of specified quality produced from specific germplasm, such as the FiberMax® Certification Program (www.certifiedfibermax.com). The capacity to track source and/or origin in mature and/or processed fibers also allows identification of plant fibers which have special characteristics, such as the fibers with improved chemical reactivity or dyeability as described in WO2006/136351.

Existing certification programs are based on recordation by growers or seed retailers of purchase of seeds of specific germplasm of a fiber crop, such as cotton, and identification of the produced fibers of the registered growers (in the case of cotton by permanent USDA bale identification numbers).

The ability to track source and/or origin of plant fibers, particularly of mature and/or processed fibers would be greatly improved if it would be possible to extract biological macromolecules from mature and or processed plant fibers which contain biological information related to the source plant of the fibers, such as peptides, proteins, nucleic acids, DNA or RNA. In this way, auditing of existing certification programs would be made possible. Additionally it would become possible to identify fibers at a later stage in the supply chain, beyond the growers or suppliers of fibers, such as e.g. at spinner, weaver or retail customer level.

Agricultural Research Service, USDA and Applied DNA Sciences worked together to develop a tagging system based on DNA embedded technologies to trace US-sourced cotton and textile components.
(on the worldwide web at seedquest.com/News/releases/2004/February/7829.htm).

It would thus be advantageous to be able to extract naturally occurring biological macromolecules from plant fibers, such as cotton fibers, particularly from mature and/or processed fibers, textiles, yarns or apparel, and further to be able to derive plant source related information from such plant fibers.

The methods described hereinafter in the different embodiments, examples, figures and claims provide a solution to the above mentioned problem, by allowing to extract natural biological macromolecules from plant fibers, such as cotton fibers, particularly from mature and/or processed fibers, textiles, yarns or apparel, and further to be able to derive plant source related information from such plant fibers.

SUMMARY OF THE INVENTION

In one embodiment, the invention provides a method for characterizing a mature plant fiber or a processed plant fiber, such as a seed fiber or cotton fiber comprising the steps of isolating from said plant fiber a biological macromolecule naturally occurring in said plant fiber other than polysaccharides or lignin; and characterizing the information encoded in the sequence of the monomers of said biological macromolecule.

In another embodiment of the invention, the invention provides a method for identifying a mature plant fiber or a processed plant fiber, such as a seed fiber or cotton fiber comprising the steps of isolating from said plant fiber a biological macromolecule naturally occurring in said plant fiber other than polysaccharides or lignin; and subjecting said biological macromolecule to a detection assay specific for said plant fiber.

In one embodiment the biological macromolecule may be a polypeptide, protein, nucleic acid, DNA, RNA, single stranded RNA or double-stranded RNA.

In another embodiment the detection assay may be a polymerase chain reaction based detection assay, an antibody based detection assay, or a nucleic acid hybridization based detection assay.

In yet another embodiment, the detection assay may detect the presence or absence of chimeric genes present in the genome of the plant producing the fibers. The chimeric gene may comprise a coding region or part or an antisense portion thereof selected from N-acetylglucosamine transferase, phosphinotricinacetyltransferase, EPSPS, hydroxyphenylpyruvatedioxygenase, an insecticidal portion of *Bacillus thuringiensis* crystal protein, poly(ADP-ribose) polymerase, poly(ADP-ribose) glucohydrolase, sucrose synthase, sucrose phosphate synthase, glucanase, cellulose synthase, chitinase, expansin, callose synthase, kinase, nicotinamidase, nicotinate phosphoribosyltransferase, nicotinic acid mononucleotide adenyl transferase, nicotinamide adenine dinucleotide synthetase or nicotine amide phosphorybosyltransferase. The detection assay may also be an event-specific detection assay.

In still another embodiment of the invention, the detection assay may detect the presence or absence of specific alleles present in the genome of the plant producing the fibers.

In yet another embodiment of the invention, the fiber from which the biological macromolecule is isolated is present in yarns, fabric, tissue or finished apparel.

The invention further provides a method for analyzing the genome of a fiber producing plant comprising the steps of isolating nucleic acids from mature or processed fibers of said plant, said nucleic acids being naturally occurring in said plant fiber; and subjecting said nucleic acid to a genome analysis protocol. The method may be applied to old mature fibers, or old yarns, fabrics or finished apparel.

Yet another embodiment of the invention is a method for isolating nucleic acid such as DNA from mature plant fibers or processed plant fibers comprising the steps of incubating said plant fibers in a buffer containing detergents, proteases and salts for a prolonged time, preferably for a period of 4 to 100 hours; and processing said lysis buffer according to standard nucleic acid isolation methods and isolating said DNA.

In another embodiment of the invention, a method is provided for isolating nucleic acid, such as DNA, from woven or knitted fabric comprising the steps of unweaving the threads of said fabric; incubating said threads in a buffer containing detergents, proteases and salts for a prolonged time, preferably for a period of 4 to 100 hours; and processing said lysis buffer according to standard nucleic acid isolation methods and isolating said nucleic acid.

In yet another embodiment of the invention, a method is provided for isolating nucleic acid, such as DNA, from harvested mature plant fibers comprising the steps of removing leaf and stem trash material from the harvested mature plant fibers; incubating said plant fibers in a buffer containing detergents, proteases and salts for a prolonged time, preferably for a period of 4 to 100 hours; and processing said lysis buffer according to standard nucleic acid isolation methods and isolating said nucleic acid.

The invention also provides for the use of a method according to the invention in a process to certify the identity of traded plant fibers.

The invention further provides a method to determine the relative amounts of different plant fibers in a mixture of mature or processed plant fibers comprising the steps of isolating from said mixture of plant fibers a biological macromolecule naturally occurring in said plant fibers other than polysaccharides or lignin; subjecting said biological macromolecule to detection assays specific for each of said plant fibers; and determining the relative amount of each of the fibers.

In another embodiment of the invention, a method is provided to certify the identity of traded cotton fibers, said method comprising recording purchase of certified cotton seeds by registered growers, said cotton seed comprising a specific genome composition and producing a particular brand of cotton fibers; registering bales of raw cotton fibers produced by said registered growers from said certified cotton seed as said particular brand of cotton fibers; authenticating said bales by cross checking with said seed purchase records; providing said registered bales to mills to produce yarns, fabrics or apparel from said brand of cotton fibers, preferably predominantly, particularly exclusively from said brand of cotton fibers; and auditing the identity of said brand of cotton fibers at one or more steps using a protocol as herein described.

DETAILED DESCRIPTION OF EMBODIMENTS OF THE INVENTION

Figure 1:
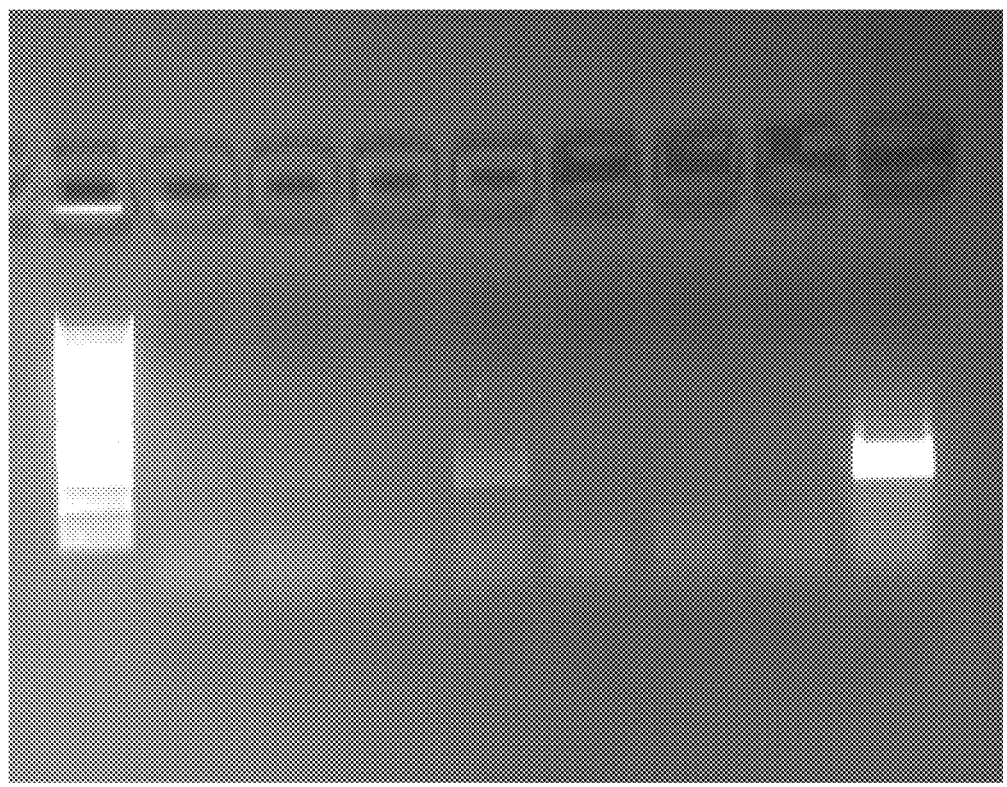
FIG. 1: PCR amplification of GhGluc1 on nucleic acids templates isolated from mature cotton fiber material (*Gossypium hirsutum* FM966). Lane 1: molecular weight marker; lane 2: template DNA from purified fibers (1 µl); lane 3: template DNA from unpurified fibers containing leaf trash (1 µl); lane 4: template DNA from leaf trash only (1 µl); lane 5: template DNA from purified fibers (5 µl); lane 6: template DNA from unpurified fibers containing leaf trash (5 µl); lane 7: template DNA from leaf trash only (5 µl); lane 8: no template control; lane 9: positive control—genomic DNA isolated from FiberMax966 (FM966) plant material.

The currently described methods are based on the unexpected finding that it is possible to extract biological macromolecules (other than polysaccharides) such as peptides, proteins, nucleic acids, DNA or RNA from mature and/or processed plant fibers, particularly from seed fibers such as cotton fibers. Moreover, the isolated DNA proved to be of sufficient quality to be usable for further processing allowing characterization of the fibers e.g. using detection assays, such as polymerase chain reaction based amplifications.

Thus, in a first embodiment, the invention provides a method for a mature plant fiber or a processed plant fiber comprising the steps of isolating from said plant fiber a biological macromolecule naturally occurring in said plant fiber other than polysaccharides or lignin; and characterizing the information encoded in the sequence of the monomers of said biological macromolecule.

As used herein, a "mature plant fiber" is a fiber which has completed its developmental cycle and is considered to be the remnant of a dead cell. In particular, a mature plant fiber is a plant fiber after it has been harvested from the fiber crop producing the plant fiber. For cotton e.g., a mature fiber would be considered the fibers as they are present in the cotton balls picked at harvest. It will be clear that a mature plant fibers comprises all plant fibers processed by the fiber industry.

A "processed plant fiber" as used herein, is a mature plant fiber as harvested from the plant crop, which has undergone additional mechanical, heat and/or chemical treatments including waxing, dying, carding, spinning, weaving, sizing, mercerization etc. (see background section).

"Plant fibers", as used herein, are long narrow tapering cells of plant origin, dead and hollow at maturity with a rigid thick cell wall composed mostly of cellulose and lignin.

"Seed fibers" as used herein are fibers grown from the surface of seeds such as cotton. "Cotton" as used herein includes *Gossypium hirsutum* or *Gossypium barbadense* including "Cotton progenitor plants" such as *Gossypium arboreturn, Gossypium herbaceum* and *Gossypium raimondii* and *Gossypium longicalyx*.

A "biological macromolecule naturally occurring in a plant fiber cell" is a biological macromolecule which has not been added exogenously to said plant fiber, e.g. through incubation or injection with a molecule such as a foreign DNA molecule, peptide or protein to tag the plant fibers, and which includes all macromolecules, i.e. molecules of polymeric nature which have an informational content. The informational content will usually be encoded in the sequence of the building blocks or monomers. Examples of biological macromolecules are polypeptides, proteins, nucleic acids such as DNA or RNA, be they single-stranded or double stranded.

"Characterizing a biological macromolecule" as used herein means to decode the informational content of the biological macromolecule. This can be conveniently done by subjecting the biological macromolecule to a series of analyses, including determining the sequence of monomers of which the macromolecule is composed, but also subjecting the biological macromolecule to one or more specific detection assays.

A "detection assay" as used herein is a method or protocol targeted at finding a specific sequence of monomers in a biological macromolecule. This may include detection assays based on polymerase chain reaction based amplification, antibody detection or nucleic acid hybridization.

It has been demonstrated that the particular extraction methods, while having an influence on the quality of the extracted biological macromolecule are not critical to the ability of being able to extract such biological macromolecules from plant fibers.

Nevertheless, it has been unexpectedly found that the quality and/or the quantity of the biological macromolecules, particularly the nucleic acid fraction thereof, isolated from mature and/or processed plant fibers can be greatly by several measures.

It may e.g. be advantageous to leave the plant fibers to be analyzed for a prolonged time in a lysis buffer containing detergents and possibly other constituents. In particular it has been found that incubating mature and/or processed plant fibers for a period of at least 30 minutes, but more preferably for a period of at least 4 hrs up to 120 hrs in a lysis buffer, preferably at room temperature will improve the yield of recovered biological macromolecules, particularly the nucleic acid fraction thereof.

It has also be determined that carefully removing impurities, including leaf remnants, resins and other trashes from the plant fibers, such as harvested and/or ginned cotton fibers, prior to isolation of the biological macromolecules, greatly improves the quality of the isolated nucleic acids, particularly with regard to further analysis and processability of the isolated nucleic acids The methods of the current invention can be advantageously used to identify cotton fibers derived from plants containing transformation events, or combination of transformation events, that may be the subject of petitions for non-regulated status, in the United States of America, to the Animal and Plant Health Inspection Service (APHIS) of the United States Department of Agriculture (USDA) whether such petitions are granted or are still pending, including the following events:

| Transformation event | Petition | Transgenic phenotype |
|---|---|---|
| COT67B | 07-108-01p | leptidopteran resistant |
| GHB614 | 06-332-01p | glyphosate tolerant |
| MON88913 | 04-086-01p | glyphosate tolerant |
| COT102 | 03-155-01p | lepidopteran resistant |
| 281-24-236 | 03-036-01p | lepidopteran resistant |
| 3006-210-23 | 03-036-02p | lepidopteran resistant |
| LLCotton25 | 02-042-01p | phosphinotricin tolerant |
| MON15985 | 00-342-01p | lepidopteran resistant |
| 31807&31808 | 97-013-01p | bromoxynil tolerant & |
| 19-51a | 95-256-01p | lepidopteran resistant Sufonylurea tolerant |
| MON 1445, 1698 | 95-045-01p | glyphosate tolerant |
| MON 531, 757, 1076 | 94-308-01p | lepidopteran resistant |
| BXN | 93-196-01p | bromoxynil tolerant |

To this end the biological macromolecules, particularly the nucleic acid such as DNA may be subjected to a detection assay specifically designed to detect the transformation events. Such detection assays include the assays published online at gmo-crl.jrc.it/statusofdoss.htm at least for events MON1445, MON531, MON15985, LLCotton25, 3006-210-23 and 281-24-236. Additional information such as nucleotide sequences of the plant flanking sequence adjacent to the inserted DNA in these transformation events (upon which information specific DNA detection assays can be designed) can be found in the following patent applications:

| Event name | Phenotype | Patent application |
|---|---|---|
| CE43-67B | Insect resistance (Cry1Ab) | WO2006/128573 |
| CE46-02A | Insect resistance (Cry1Ab) | WO2006/128572 |
| CE44-69D | Insect resistance (Cry1Ab) | WO2006/128571 |
| 1143-14A | Insect resistance (Cry1Ab) | WO2006/128569 |
| T342-142 | Insect resistance (Cry1Ab) | WO2006/128568 |
| event3006-210-23 | Insect resistance (Cry1Ac) | WO2005103266 |
| PV-GHGTO7 (1445) | Glyphosate tolerance | US2004-148666 |
| MON88913 | Glyphosate tolerance | WO2004/072235 |
| EE-GH3 | Glyphosate tolerance | WO2007/017186 |
| T303-40 | Insect-resistance | PCT/EP2008/002667 |
| GHB119 | Insect-resistance | PCT/EP2008/004652 |
| Cot202 | Insect resistance (VIP3) | US2007-067868 |
| LLcotton25 | Glufosinate resistance | WO2007/017186 |
| event 281-24-236 | Insect resistance (Cry1F) | WO2005103266 |
| Cot102 | Insect resistance (Vip3A) | US2006-130175 |
| MON15985 | Insect resistance | US2004-250317 |

The methods of the current invention can be advantageously used to identify cotton fibers derived from cotton plants containing genetic material which imparts particularly advantageous, useful traits to these plants. Examples of such traits are better plant growth, increased tolerance to abiotic stresses such as high or low temperatures, drought, extreme water or salt or mineral content in the soil, increased flowering performance, easier harvesting, accelerated maturation, higher harvest yields of commercially relevant plant parts (e.g. seeds), higher quality and/or a higher nutritional value of the harvested products, better storage stability and/or processability of the harvested products. Further and particularly emphasized examples of such traits are resistance against biotic stresses i.e. a better defense of the plants against animal and microbial pests, such as against insects, mites, phytopathogenic fungi, bacteria and/or viruses, and also increased tolerance of the plants to certain herbicidally active compounds.

The methods of the current invention can be advantageously used to identify cotton fibers derived from cotton plants containing genetic material which imparts herbicide-resistance for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, Wo 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665. Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 96/38567, WO 99/24585 and WO 99/24586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme prephenate deshydrogenase in addition to a gene encoding an HPPD-tolerant enzyme, as described in WO 2004/024928. Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/ 106529, WO 2005/020673, WO 2005/093093, WO 2006/ 007373, WO 2006/015376, WO 2006/024351, and WO 2006/ 060634. Further sulfonylurea- and imidazolinone-tolerant plants are also described in for example WO 07/024,782.

The methods of the current invention can be advantageously used to identify cotton fibers derived from cotton plants containing genetic material which imparts resistance to attack by certain target insects. Such plants can be obtained by genetic transformation, or by selection of plants containing a mutation imparting such insect resistance and may contain at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/ 027777); or 4) a protein of any one of A1) to A3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed online at: www.lifesci.sussex.ac.uk/home/ Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

The methods of the current invention can be advantageously used to identify cotton fibers derived from cotton plants containing genetic material which imparts tolerance to abiotic stresses. Such plants can be obtained by genetic transformation and may contain one or more of the following transgenes a. a transgene capable of reducing the expression and/or the activity of poly(ADP-ribose)polymerase (PARP) gene in the plant cells or plants as described in WO 00/04173 or EP 04077984.5 or EP 06009836.5.

b. a stress tolerance enhancing transgene capable of reducing the expression and/or the activity of the PARG encoding genes of the plants or plants cells, as described e.g. in WO 2004/090140.

c. a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7 or WO 2006/133827 or PCT/EP07/002, 433.

The methods of the current invention can be advantageously used to identify cotton fibers derived from cotton plants containing genetic material which can modify the characteristics of the fiber such as strength, length, micronaire etc. including the chimeric genes described in WO05/017157 (glucanase silencing genes) WO04/0655571 (chitinase encoding genes), WO02/45485 and WO08/012,058 (sucrose synthase genes), WO01/17333 (sucrose phosphate synthetase genes) WO98/00549 (cellulose synthase genes) WO06/133827 (N-acetylglucosamine transferase genes such a chitin synthase or NODC encoding genes).

A further application for the methods of the current invention is to identify plant fibers, such as cotton fibers from plants which comprise specific allelic variations of particular genes. The methods for identifying such allelic variations are well known in the art. In particular, such allelic variations may be used to differentiate between fibers from particular plant species such as e.g. differentiating between fibers from *G. barbadense* and *G. hirsutum*. As an example, the polymorphism between glucanase1 A subgenome allele from *Gossypium barbadense* and from *Gossypium hirsutum* (by the presence of a stop codon in the coding region of Gluc1 A subgenome allele in *G. barbadense*, as described in unpublished EP application 08075514.3 herein incorporated by reference) may be used to differentiate fibers originating from *Gossypium barbadense* or *Gossypium hirsutum*.

The methods herein described may also be used to isolate nucleic acid templates which can be used for any genome characterization protocols, including AFLP, READS and the like. The nucleic acid templates isolated from the mature or processed fibers, may be amplified using methods known in the art such as whole genome amplification, prior to application of a genome characterization protocol.

The methods described herein may also be used to assist in certification programs, guaranteeing the supply of commercially traded plant fibers, such as cotton fibers, having particularly specified characteristics. Usually, such certification programs include recordation of the purchase of certified seeds by registered growers, whereby the cotton seed comprise a specific genome composition and produce a particular brand of plant fibers. Balese of the harvested plant fibers produced by the registered growers from the said certified seeds are registered and authenticated by cross checking with said seed purchase records and are provided to mills to produce preferably predominantly, particularly exclusively yarns, fabrics or apparel from said brand of fibers. The methods describe herein allow to perform audits at different points in the supply chain.

The methods described herein can also be applied to isolate biological macromolecules from hair-like (trichome-like) structures on plant seeds, such as the hairs on tomato seeds or the bear hairs on the basis of wheat seeds.

The methods described herein can also be applied to characterize the nucleic acid material of old fibers and old textile material (e.g. fibers and textiles which are over 100 years old). Without limiting the invention to a specific mechanism or theory it is believed that one possibility that biological material is preserved in old fibers is because we have observed that mature fibers are twisted such that biological material is 'trapped' (and thereby 'preserved') in mature fibers.

The methods described herein can also be applied in forensic applications because fiber or textile material identified at a crime scene can be characterized by for example preceding a whole genome amplification step as shown in example 6 in this application.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The following non-limiting Examples describe the methods for isolating biological macromolecules from mature plant fibers and from processed fibers and their use for characterizing or identifying plant fibers. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:

SEQ ID No 1: oligonucleotide 1 for PCR amplification of Ghgluc1
SEQ ID No 2: oligonucleotide 2 for PCR amplification of Ghgluc1
SEQ ID No 3: oligonucleotide 1 for PCR amplification of NodC
SEQ ID No 4: oligonucleotide 2 for PCR amplification of NodC
SEQ ID No 5: oligonucleotide 1 for PCR amplification of expansin
SEQ ID No 6: oligonucleotide 2 for PCR amplification of expansin
SEQ ID No 7: oligonucleotide 1 for Taqman detection assay of GhGluc1 (forward primer)
SEQ ID No 8: oligonucleotide 2 for Taqman detection assay of GhGluc1 (reverse primer)

SEQ ID No 9: oligonucleotide 3 for Taqman detection assay of subenomic A GhGluc1 allele (VIC marked oligonucleotide detecting the *G. hirsutum* allele of Gluc1)

SEQ ID No 10: oligonucleotide 4 for Taqman detection assay of subenomic A GhGluc1 allele (FAM marked oligonucleotide detecting the *G. barbadense* allele of Gluc1)

SEQ ID No 11: oligonucleotide 1 for PCR amplification of rpl16

SEQ ID No 12: oligonucleotide 2 for PCR amplification of rpl16

SEQ ID No 13: oligonucleotide 1 for PCR amplification of matK

SEQ ID No 14: oligonucleotide 2 for PCR amplification of matK

SEQ ID No 15: oligonucleotide 1 for PCR amplification of trnT-tmL

SEQ ID No 16: oligonucleotide 2 for PCR amplification of trnT-tmL

SEQ ID No 17: oligonucleotide 1 for PCR amplification of ndhF

SEQ ID No 18: oligonucleotide 2 for PCR amplification of ndhF

EXAMPLES

Example 1

Isolation of Nucleic Acids from Raw Cotton Fiber Material

A. Isolation of Nucleic Acids from *Gossypium hirsutum* FM966 Fiber Material.

Harvested cotton fibers from FM966, which had been ginned and baled, were subjected to DNA extraction using the conventional CTAB (Hexadecyl trimethyl-ammonium bromide) procedure (Doyle and Doyle, 1987, Phytochem. Bull. 19, 11) for isolation of genomic DNA from plant material. Although a pellet of nucleic acids was obtained, this material could not be used for any further application including PCR amplification, or restriction enzyme digestion.

The harvested baled raw cotton fibers still contain some impurities such as leaf remnants and other trashes. These contaminant materials were carefully removed by manual cleaning to obtain a purified fiber fraction (and a trash fraction). The raw fiber material, the purified fiber material and the trash fraction were subjected to DNA extraction using the DNeasy®Plant Mini Kit commercialized by QIAGEN according to the manufacturer's recommendations (see DNeasy® Plant Handbook available at www1.qiagen.com/HB/DNeasyPlantMiniMaxi) and the concentrations of the isolated nucleic acids was determined using UV spectrophotometry (Table 1)

TABLE 1

| Sample | ng/ul | A260 | A280 | 260/280 | 260/230 |
|---|---|---|---|---|---|
| Pure fiber | 3.49 | 0.07 | 0.05 | 1.41 | 0.52 |
| Pure fiber | 4.19 | 0.084 | 0.065 | 1.29 | 0.51 |
| Raw fiber | 14.91 | 0.298 | 0.194 | 1.54 | 0.43 |
| Raw fiber | 17.4 | 0.348 | 0.239 | 1.46 | 0.43 |
| Trash only | 76.55 | 1.531 | 1.09 | 1.4 | 0.45 |

The isolated nucleic acids were used as templates in a standard PCR reaction using the following primers to detect an endogenous cotton glucanase gene (GhGluc1; see EP 08075514.3 herein incorporated by reference for nucleotide sequences of different alleles of GhGluc1):

SE002: ggccgaagccgatcttatctagg (SEQ ID No.: 1)
SE003: cggcaacaatcttccatctccag (SEQ ID No.: 2)

Both 1 µl and 5 µl of template nucleic acids were used. The results of the PCR amplification are visualized in FIG. 1. A 656 bp amplicon (as expected) is clearly detected using pure fiber (5 µl template) (lane 4) whereas a faint signal can be observed using small amount (1 µl) of nucleic acids isolated from both pure and raw fiber material. No amplification signal can be detected in the nucleic acids isolated from the trash material only nor from the nucleic acids obtained from unpurified material when used in higher concentrations indicating that the extract obtained from contaminant materials appears to inhibit the further processing of nucleic acids obtained from raw fiber material.

Interestingly, this experiment demonstrates that nucleic acids, which can be further analyzed, can be extracted from mature cotton fiber material. The experiment also indicates that the quality of the isolated nucleic acids—DNA can be further improved by removing the leaf trash and other impurities from the raw harvested and ginned cotton fibers.

B. Isolation of Nucleic Acids from *Gossypium barbadense* Pima-Y5 Fiber Material.

Figure 2:
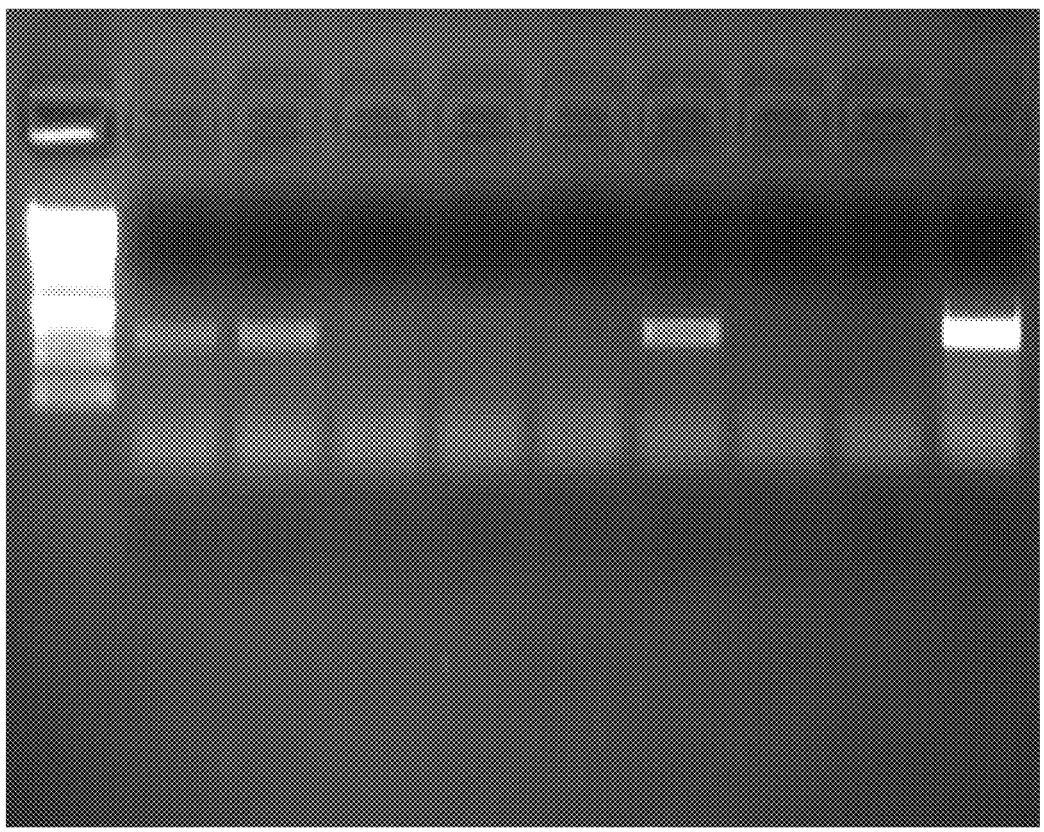
FIG. 2: PCR amplification of GhGluc1 on nucleic acids templates isolated from mature *Gossypium hirsutum* FM966 cotton fiber material and from 4 year old *Gossypium barbadense* Pima Y5 cotton fiber material. Lane 1: molecular weight marker; lanes 2-3: template DNA from FM966 purified fibers containing no leaf trash (5 µl); lanes 4-5: template DNA from FM966 unpurified fibers containing leaf trash (5 µl); lane 6: template DNA from FM966 leaf trash containing no fiber material (5 µl); lanes 7-8: template DNA from Pima Y5 purified fibers containing no leaf trash (5 µl); lane 9: no template control; lane 10: positive control—genomic DNA isolated from FiberMax966 plant material.

4 year old raw cotton fiber material from *Gossypium barbadense* Pima5Y was treated along with *Gossypium hirsutum* FM966 cotton fiber material, as described above in 1.A. The obtained nucleic acids were used as templates in PCR reactions as described in 1.A. The results are visualized in FIG. 2.

Although *Gossypium barbadense* fibers are stronger and have a different architecture from *Gossypium hirsutum* fibers, the results demonstrate that nucleic acids including processable DNA can also be isolated from these fibers. Interestingly, these fibers had also been stored for several years under non-optimal conditions indicating that processable DNA or other nucleic acids can be obtained from old fiber material.

C. Amplification of Other Cotton Endogenous Genes.

The isolated nucleic acids were also used as templates in standard PCR reactions using primers specific for other endogenous genes such as the following primers which amplify a 299 bp fragment from the expansin encoding gene:

```
K151:
gggagcttgtggttatggaaacc      (SEQ ID No.: 5)

K152:
cagggacgatcccagctcgatattc    (SEQ ID No.: 6)
```

The expected amplicons could also be detected using these other primers for other endogenous genes.

D. Isolation of Nucleic Acids from Cotton Fiber Material Using Other Lysis Buffers and Protocols.

Raw cotton fiber material was purified as described in section 1.A. by removing the contaminating leaf trash material and other impurities. Nucleic acids were extracted from the purified fiber material using either the DNeasy® Plant Mini Kit commercialized by QIAGEN or the Wizard® Genomic DNA Purification Kit commercialized by PROMEGA CORPORATION or the conventional CTAB procedure (Doyle and Doyle, 1987, Phytochem. Bull. 19, 11). The concentration of the obtained nucleic acids was determined using U.V. spectrophotometry (Table 2).

TABLE 2

| Sample | ng/ul | A260 | A280 | 260/280 | 260/230 |
|---|---|---|---|---|---|
| Qiagen 1 | 7.66 | 0.153 | 0.069 | 2.21 | 1.4 |
| Qiagen 2 | 19.97 | 0.399 | 0.241 | 1.66 | 0.76 |

TABLE 2-continued

| Sample | ng/ul | A260 | A280 | 260/280 | 260/230 |
|---|---|---|---|---|---|
| Promega 1 | 21.34 | 0.427 | 0.208 | 2.05 | 1.42 |
| Promega 2 | 38.14 | 0.763 | 0.389 | 1.96 | 1.06 |
| CTAB* | 225.22 | 4.504 | 2.235 | 2.02 | 1.42 |

*Note: High concentration readings probably due to absence of RNAse treatment.

The isolated nucleic acids were used as templates in a standard PCR reaction using the following primers to detect an endogenous cotton glucanase gene (GhGluc1; see EP 08075514.3 herein incorporated by reference for nucleotide sequences of different alleles of GhGluc1):

```
SE002:
ggccgaagccgatcttatctagg      (SEQ ID No.: 1)

SE003:
cggcaacaatcttccatctccag      (SEQ ID No.: 2)
```

Figure 3:
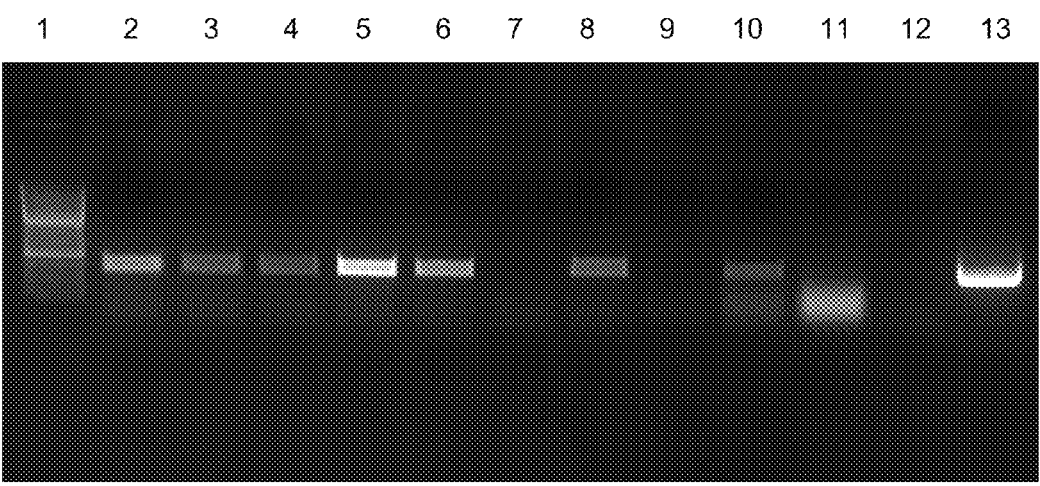
FIG. 3: PCR amplification of GhGluc1 on nucleic acids templates isolated through various protocols. Lane 1: molecular weight marker; lane 2: template DNA isolated by DNeasy® Plant Mini Kit (5 µl); lane 3: template DNA isolated by DNeasy® Plant Mini Kit (1 µl); lane 4: template DNA isolated by DNeasy® Plant Mini Kit (1 µl); lane 5: template DNA isolated by DNeasy® Plant Mini Kit (5 µl); lane 6: template DNA isolated by Wizard® Genomic DNA Purification Kit (1 µl); lane 7: template DNA isolated by Wizard® Genomic DNA Purification Kit (5 µl); lane 8: template DNA isolated by Wizard® Genomic DNA Purification Kit (1 µl); lane 9: template DNA isolated by Wizard® Genomic DNA Purification Kit (5 µl); lane 10: template DNA isolated by CTAB-procedure (1 µl); lane 11: template DNA isolated by CTAB procedure (5 µl); lane 12: no template control; lane 13: positive control—genomic DNA isolated from FiberMax966 plant material.

Both 1 µl and 5 µl of template nucleic acids were used. The results of the PCR amplification are visualized in FIG. 3. The expected DNA amplicon was observed using template nucleic acids isolated by any method, although apparently higher concentrations of the nucleic acids (5 µl reaction) isolated by Wizard® and CTAB procedures had a negative effect on the PCR reaction.

Albeit with a lower efficiency, we observed that nucleic acids could also be extracted from the cleaned fiber material by incubating this fiber material with water ($H_2O$) for a certain amount of time (e.g. at least 4 hours incubation of the cleaned fiber material in the presence of a volume of water).

Example 2

Isolation of Nucleic Acids from Textiles

A. Isolation of Nucleic Acids from Cotton Cloth.

The successful isolation of nucleic acids, such as DNA which can be further processed, from mature cotton fibers, spurred an attempt to isolate biological macromolecules such as nucleic acids, particularly processable DNA from fibers after spinning and weaving. To this end, yarns were isolated by unweaving a piece of cotton cloth, cut into smaller pieces and incubated in 5 ml of lysis buffer (DNeasy® AP1 buffer) at 65° C. for at least 30 minutes or overnight at room temperature. Buffer was squeezed out of the material and 500 µl lysate was transferred to an eppendorf tube and further treated according to the manufacturer's recommendations i.e.:

- add 130 µl AP2 buffer, mix and incubate on ice for 5 minutes
- centrifuge for 5 minutes at 13000 rpm
- transfer the liquid phase to the lilac QIAshredder mini spin column
- centrifuge for 2 minutes at 13000 rpm
- transfer the flow through to a new eppendorf tube without disturbing the pellet;
- add 800 µl AP3/E buffer and mix
- transfer 650 µl to the DNeasy® mini spin column and centrifuge for 1 minute at 8000 rpm, discarding the flow-through
- repeat this step with the remaining sample; discard the collection tube and place the column in a new 2 ml collection tube
- wash the column with 500 µl AW buffer and centrifuge for 1 min at 8000 rpm, discard the flow-through
- wash the column with 500 µl AW buffer and centrifuge for 2 min at 13000 rpm, discard the flow-through
- place the column in a 1.5 ml eppendorf without ethanol carryover.
- Add 50 W water to the column and incubate at least 5 minutes at room temperature
- Centrifuge for 1 minute at 8000 rpm. Store the DNA at 4° C.

Figure 4:
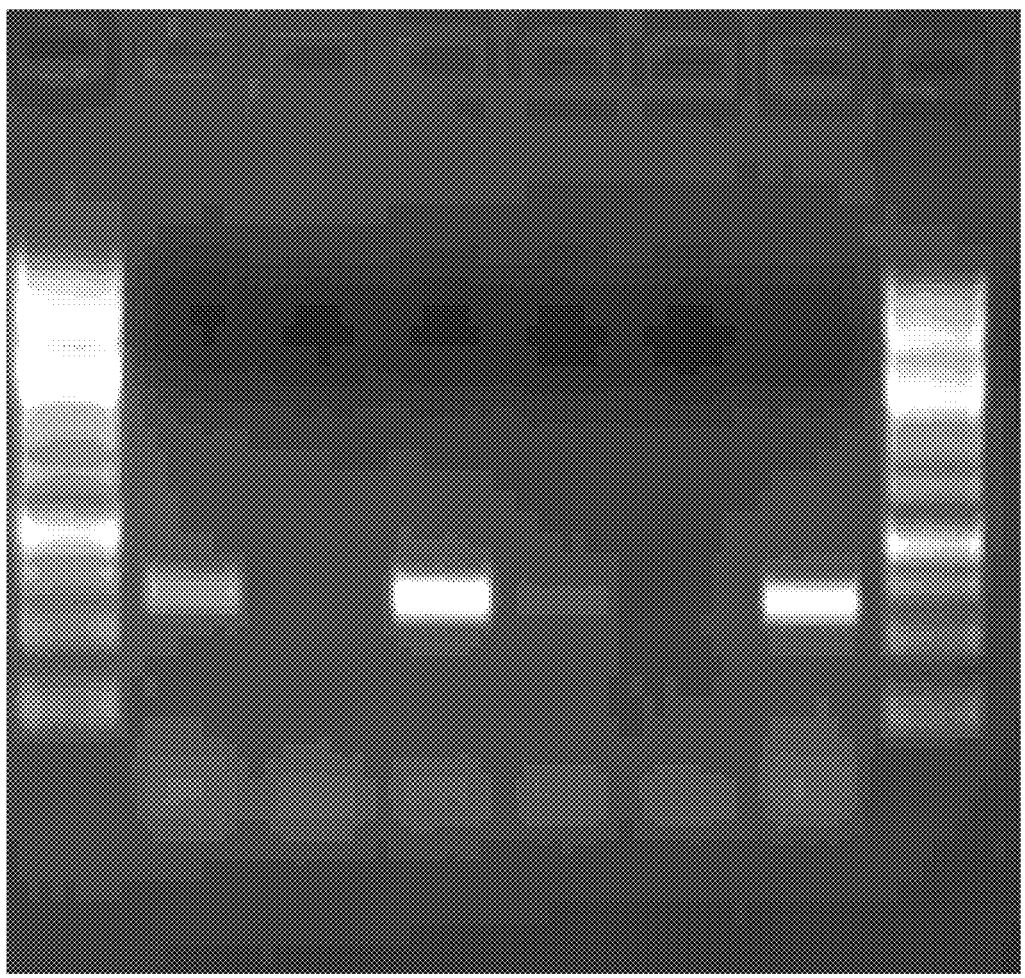
FIG. 4: PCR amplification of GhGluc1 on nucleic acids templates isolated cotton cloth. Lanes 1 and 8: molecular weight marker; lane 2: template DNA from cotton cloth (ON incubation) (1 µl); lane 3: template DNA from cotton cloth (30' incubation) (1 µl); lane 4: template DNA from cotton cloth (ON incubation) (5 µl); lane 5: template DNA from cotton cloth (30' incubation) (5 µl); lane 6: no template control; lane 7: positive control—genomic material isolated from FiberMax966 plant material.

1 and 5 µl samples were used as template DNA in a PCR reaction using the primers of example 1.A. The results are visualized in FIG. 4. When nucleic acid samples after overnight incubation were used, the expected amplicon of 669 bp could be detected, indicating that the protocol can be used to isolate nucleic acids from cotton fibers after spinning and weaving. The significantly stronger PCR signal after overnight incubation versus the 30 minutes incubation, indicates the former protocol results in higher concentration of processable DNA.

B. Isolation of Nucleic Acids from Textiles with Different Weaves.

Figure 5:
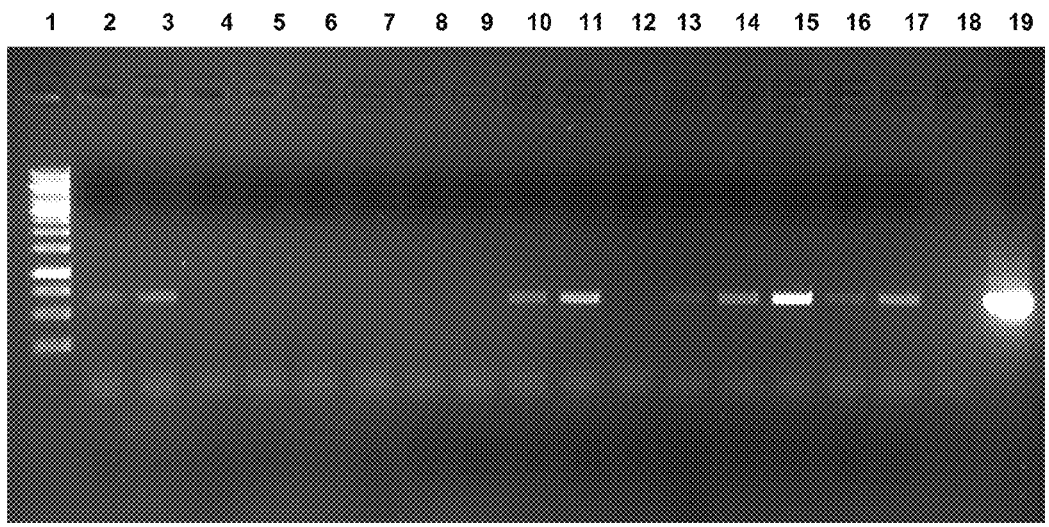
FIG. 5: PCR amplification of GhGluc1 on nucleic acids templates isolated from cotton shirts with different weaves (knitted or woven). Lane 1: molecular weight marker; lane 2: template DNA from woven cotton shirt, ON incubation, (1 µl); lane 3: template DNA from woven cotton shirt, ON incubation, (5 µl); lane 4: template DNA from woven cotton shirt, ON incubation, (1 µl); lane 5: template DNA from woven cotton shirt, ON incubation, (5 µl); lane 6: template DNA from knitted cotton shirt, ON incubation, (1 µl); lane 7: template DNA from knitted cotton shirt, ON incubation, (5 µl); lane 8: template DNA from knitted cotton shirt, ON incubation, (1 µl); lane 9: template DNA from knitted cotton shirt, ON incubation, (5 µl); lane 10: template DNA from woven cotton shirt, 6 days incubation, (1 µl); lane 11: template DNA from woven cotton shirt, 6 days incubation, (5 µl); lane 12: template DNA from woven cotton shirt, 6 days incubation, (1 µl); lane 13: template DNA from woven cotton shirt, 6 days incubation, (5 µl); lane 14: template DNA from knitted cotton shirt, 6 days incubation, (1 µl); lane 15: template DNA from knitted cotton shirt, 6 days incubation, (5 µl); lane 16: template DNA from knitted cotton shirt, 6 days incubation, (1 µl); lane 17: template DNA from knitted cotton shirt, 6 days incubation, (5 µl); lane 18: no template control; lane 19: positive control—genomic DNA isolated from FiberMax966 plant material.

The nucleic acid isolation protocol was also applied to finished apparel with different weaves (i.e. which has undergone different processing). To this end, pieces were cut from a cotton long-sleeve shirt (woven) and a cotton polo (knitted) and threated as in Example 2A, with the exception that incubation in lysis buffer was performed either overnight, or even prolonged to 6 days of incubation. A PCR reaction as described in Example 2.A was performed on the isolated nucleic acids and the results are visualized in FIG. 5.

The expected amplicon was detected after PCR amplification using nucleic acid samples isolated from both kinds of fabrics. Again, the signal was stronger in samples in which the incubation in lysis buffer had been prolonged.

Example 3

Isolation of Nucleic Acids from Specialty Fibers

Mature fibers were isolated and purified from transgenic cotton plants comprising an N-acetylglucosamine transferase chimeric gene ("NodC gene") as described in WO2006/136351 Example 1. Nucleic acids were isolated from the purified fibers extraction using the DNeasy®Plant Mini Kit commercialized by QIAGEN according to the manufacturer's recommendations (see DNeasy® Plant Handbook available at www1.qiagen.com/HB/DNeasyPlantMiniMaxi) and the concentrations of the isolated nucleic acids was determined using UV spectrophotometry (Table 3)

TABLE 3

| Sample | ng/ul | A260 | A280 | 260/280 | 260/230 |
|---|---|---|---|---|---|
| NodC1 | 7.95 | 0.159 | 0.105 | 1.51 | 0.56 |
| NodC2 | 7.62 | 0.152 | 0.101 | 1.51 | 0.56 |

The isolated nucleic acids were also used as templates in standard PCR reactions using primers specific for other endogenous genes such as the following primers which amplify a 1224 bp fragment from the NodC encoding gene:

```
Idb093:
                                 (SEQ ID No.: 3)
cgtttttcactcatcgtcgttttcaagtgtcgtagatgtgatcggtt
tgcttgcg
```

```
Idb126:
                                             (SEQ ID No.: 4)
ggcgcgccttaggaactctcgcgtgatagccac
```

Figure 6:
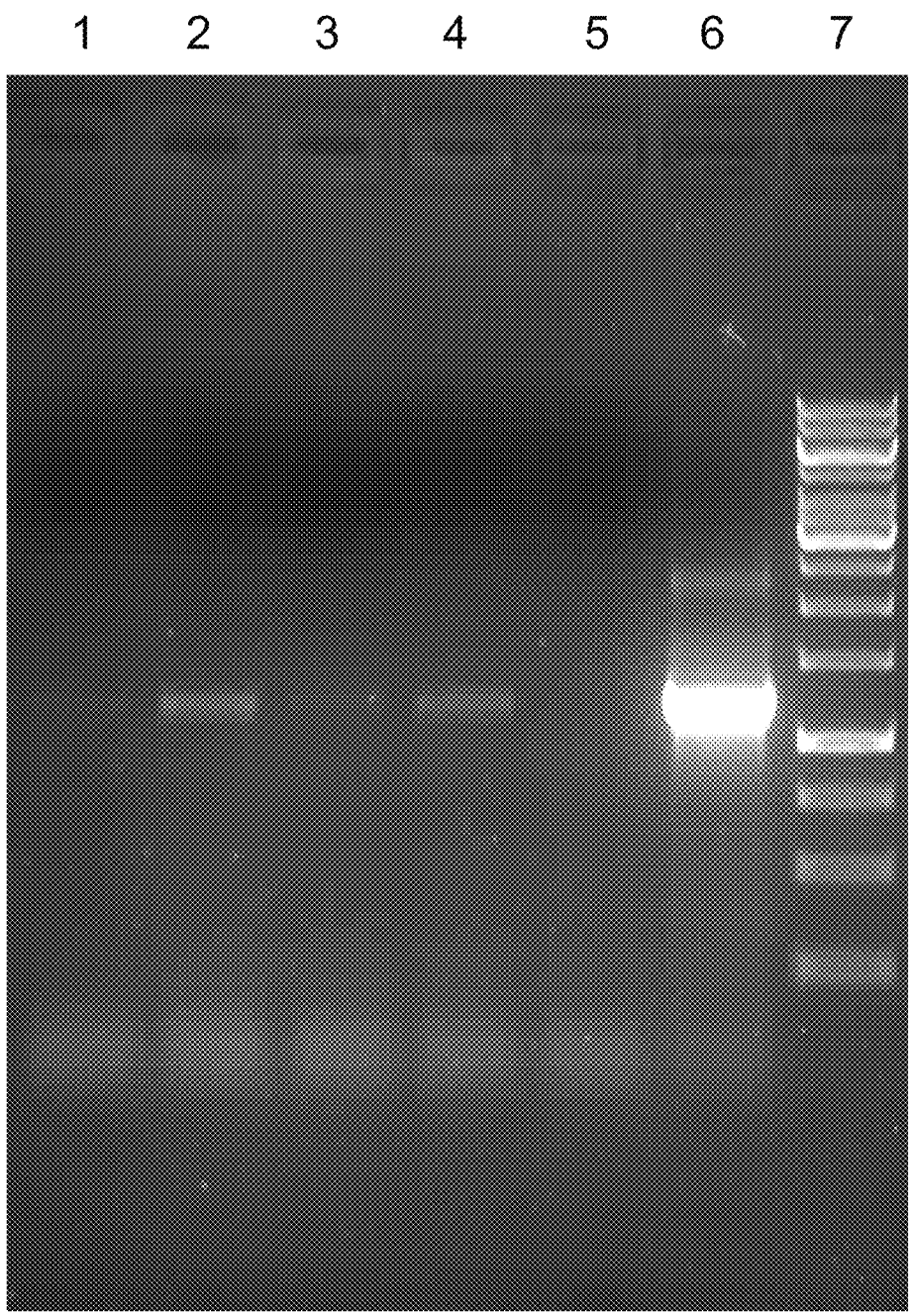
FIG. 6: PCR amplification of NodC on nucleic acids templates isolated from mature transgenic cotton fiber material containing a chimeric N-acetylglucosamine transferase encoding gene. Lane 1: template DNA from transgenic fiber material, duplicate 1 (1 µl); Lane 2: template DNA from transgenic fiber material, duplicate 1 (5 µl); Lane 3: template DNA from transgenic fiber material, duplicate 2 (1 µl); Lane 4: template DNA from transgenic fiber material, duplicate 2 (5 µl); lane 5: no template control; lane 6: positive control—genomic DNA isolated from transgenic cotton plant material; lane 7: molecular weight marker.

Both 1 µl and 5 µl of template nucleic acids were used. The results of the PCR amplification are visualized in FIG. 6. The expected DNA amplicon indicative of the presence of the transgene could be observed in each sample.

Example 4

Automation and Differentiation Between Different Fiber Types

As described in unpublished EP application 08075514.3 herein incorporated by reference, the glucanase1 A subgenome allele from *Gossypium barbadense* differs from the glucanase 1 subgenome allele from *Gossypium hirsutum* by the presence of a stop codon in the coding region of Gluc1 A subgenome allele in the former. This polymorphism could be used to differentiate between cotton fibers from plants having the *Gossypium barbadense* Gluc1 allele or the *Gossypium hirsutum* Gluc1 allele. To this end, a Taqman® assay was designed, whereby the oligonucleotide primers to amplify a DNA fragment carrying the polymorphism used were:

```
Forward primer:
GCTTTTGGAAGCGATATAACATCGA     (SEQ ID No.: 7)

Reverse primer:
GGCATAGGCAAAATAAGGGTACACA     (SEQ ID No.: 8)
```

The polymorphism was detected by the monitoring of the degradation of the following fluorescence marked primers detecting the polymorphism:

```
VIC-AATCCTGTCGAACCAG          (SEQ ID No.: 9)
(hirsutum allele)

FAM-ATCCTGTCAAACCAG           (SEQ ID No.: 10)
(barbadense allele)
```

Figure 7:
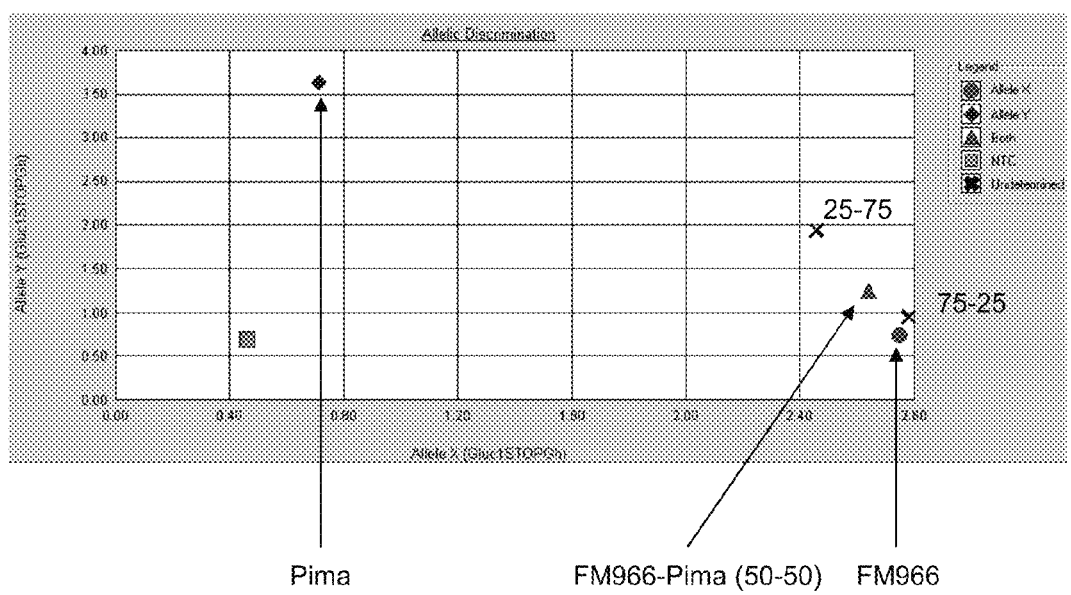
FIG. 7: Graphic representation of the endpoint Taqman assay discriminating between the GhGluc1 A subgenome allele from *Gossypium hirsutum* and from *Gossypium barbadense*. Genomic DNA samples prepared from Pima (*G. barbadense*) or FM966 (*G. hirsutum*) plant (leaf) material, either in pure form, or in mixes of various ratio's (75/25, 50/50 and 25/75), subjected to a TaqMan detection assay. The X axis indicates the presence of the *hirsutum* allele of Gluc1, while the Y-axis indicates the presence of the *barbadense* allele of Gluc1. In the mixed DNA samples, the Taqman analysis allows the detection of the various ratio's of both alleles.

These primers were used in a qPCR setup, increasing the numbers of cycles up to 60 and determining fluorescence at the endpoint only. As nucleic acid templates, mixes of DNA isolated from either *G. barbadense* fibers (PIMA) or *G. hirsutum* fibers (FM966) were used in the following ratios: 100% PIMA, 75% PIMA/25% FM966, 50% PIMA/50% FM966, 25% PIMA/75% FM966, 100% FM966. The results are schematically represented in FIG. 7.

The X axis indicates the presence of the *G. hirsutum* allele of Gluc1, while the Y-axis indicates the presence of the *G. barbadense* allele of Gluc1. In DNA isolated from PIMA fibers, only the *G. barbadense* allele of Gluc1 was detected. In DNA isolated from PIMA fibers, only the *G. hirsutum* allele of Gluc1 was detected. In the mixed DNA samples, the Taqman analysis allows the detection of the various ratio's of both alleles.

Figure 8:
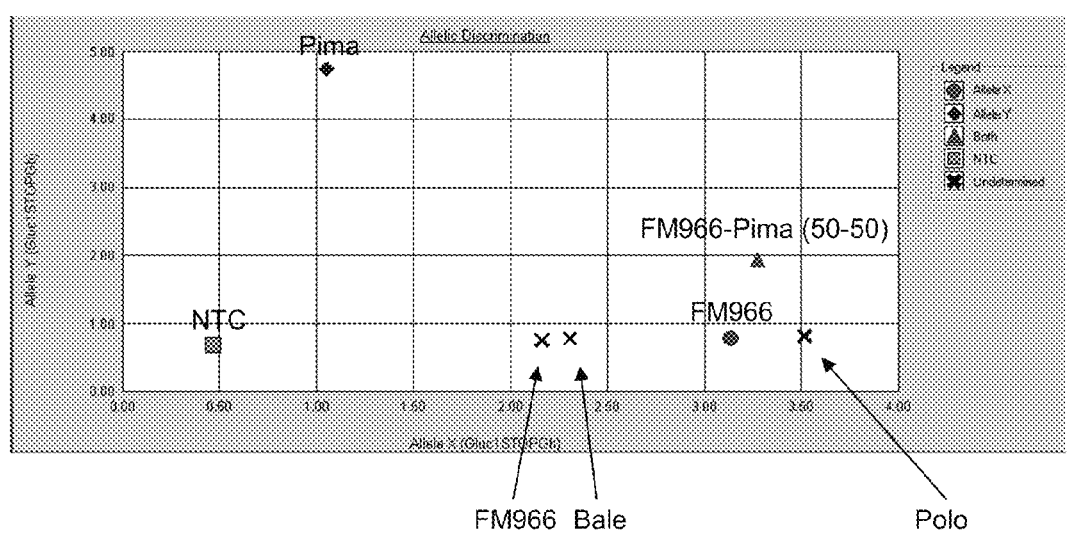
FIG. 8: Graphic representation of the endpoint Taqman assay discriminating between the GhGluc1 A subgenome allele from *Gossypium hirsutum* and from *Gossypium barbadense* on fiber material and polo shirt textile. Genomic DNA samples prepared from Pima (*G. barbadense*) or FM966 (*G. hirsutum*) plant (leaf) material, either in pure form, or in mix of 50/50 as control samples. Nucleic acids prepared from fiber material (FM966 Bale) or from textile material (polo) was subjected to a TaqMan detection assay. The X axis indicates the presence of the *hirsutum* allele of Gluc1, while the Y-axis indicates the presence of the *barbadense* allele of Gluc1. In the analysis only the *hirsutum* allele was detected, indicating that all fiber material and all textile material contains only *hirsutum* type fibers.

In a further step, the same RT-PCR type analysis was used to analyze nucleic acid samples from cotton textile and fiber material from a FM966 bale. The results are represented in FIG. 8. In nucleic acids extracted from the FM966 bale and from the polo shirts, only the *G. hirsutum* allele of Gluc1 was detected, indicating that the cotton material used exclusively originated from *G. hirsutum* type material.

Although the assays may need further optimization, such optimization is clearly within the realm of the skilled person.

Example 5

Characterization of the Plastid Genome Isolated from Cotton Fibers

Because of the unexpected finding that genomic DNA can be isolated and characterized from mature cotton fibers we investigated the possibility of identifying plastid DNA in the pool of DNA extracted from these fibers.

Although, leucoplast plastids have been shown to be present in developing cotton fibers (Ryser U. (1985) *European journal of cell biology* 39, pp. 236-256) they are not expected to be present in mature cotton fibers. Leucoplasts are similar to chloroplasts by having the same genome—because they differentiated from the same progenitor cell type—but leucoplasts are specialized with high accumulation of starch content.

Cronn et al (2002) *American Journal of Botany* 89(4): 707-725 published primer combinations to amplify 4 genes of the plastid genome (rpl16, matK, trnT-trnL and ndhF). In a first step we optimized the published primer combinations for amplification of these four genes by carrying our PCR analysis on DNA isolated from cotton leaves. In a next step, the optimized primer combination per gene was used for amplification on a fiber DNA sample obtained from a cotton mini bale (Certified FiberMax cotton). We surprisingly showed amplification of 4 PCR fragments from this fiber DNA sample. Subcloning in TOPO-blunt vectors followed by sequence analysis of these fragments confirmed that these four fragments originated from the plastid genome. For rpl16, matK and trnT-trnL the sequencing resulted in a unique consensus sequence, for ndhF several consensus sequences were obtained.

Since the complete chloroplast sequences of *Gossypium hirsutum* and *Gossypium barbadense* are available in the EMBL database (entry DQ345959 is the chloroplast DNA sequence of coker 310 FR (*G. hirsutum*) and entry AP009123 is the chloroplast DNA sequence of *G. barbadense*) it was possible to align the obtained sequences with the published sequences. It was found that the obtained sequences were 100% identical to the published *G. hirsutum* sequences (except for the degenerate primer sites). This confirms that the fiber in the cotton bale was derived from *G. hirsutum*.

The successful molecular characterization of these specific plastid sequences now provides novel opportunities for genotyping of fiber DNA. Also older fiber samples can be probed for plastid sequences and their relationship can be interpreted during evolution and breeding.

PCR Conditions:
2 µl template
1.5 µl forward primer (10 µM)
1.5 µl reverse primer (10 µM)
21 µl MQ
1 µl dNTP
10 µl 10× HF buffer
0.5 µl Phusion
12.5 µl MQ
PCR Program
30 s @ 98° C.
10 s @ 98° C.
30 s @ 60° C.
60 s @ 72° C.
35 cycli
10 min @ 72° C.
Hold @ 4° C.

Primer Combinations:

| | | |
|---|---|---|
| rp116 | F71: | gctatgcttagtgtgtgactcgtt (SEQ ID No 11) |
| | R1516: | cccttcattcttcctctatgttg (SEQ ID No 12) |
| matK | matKF3: | ctaatggatcaacagaawcgtttg (SEQ ID No 13) |
| | trnKR: | aactagtcggatggagtag (SEQ ID No 14) |
| trnT-trnL | trnL2: | aatattactgactccmttttkattttckag (SEQ ID No 15) |
| | trnB: | tctaccgatttcgccatatc (SEQ ID No 16) |
| ndhF | 5'Fnew: | gaatatgcatggatcatacc (SEQ ID No 17) |
| | 1318R: | cgaaacatataaaatgcrgttaatcc (SEQ ID No 18) |

Example 6

Characterization of the Genome of Nucleic Acids Isolated from Cotton Fibers

The previous examples have convincingly shown that DNA can be isolated and characterized from mature cotton fibers and from downstream products thereof. In a next step we questioned if the isolated fiber DNA is a true representation of the whole cotton genome or whether it represents only a fraction of the cotton genome. A partial genome equivalent would not be useful for trait or genotype testing as it would generate unreliable and incomplete assay results. The first challenge was to overcome the limited amount of DNA obtained from cotton fibers as starting material for assay testing. The method of Whole Genome Amplification (WGA) was chosen to overcome this limitation. WGA has not been used before to amplify a polyploid genome such as cotton, for genotyping and trait testing. A DNA amplification step is important to enhance the amount of starting fiber DNA material but it is critical not to introduce a genome bias which is sometimes inherent to a WGA step as reported by Giardina et al (2009) *BMC Genomics* April 14, 10:159. We addressed the reliability of a WGA step on isolated fiber DNA in a functional Taqman assay. Thereto the quality of WGA-amplified fiber DNA was compared with WGA-amplified cotyledon DNA of the same commercial cotton fiber source in substantially the same Taqman assay.

Approximately 500 grams of FM9063B2F fiber (500 grams samples each in 3 small brown bags; 3 replicates were taken from different bales for the sample variety, Bale no 721134350138, 721134350154, 721134350156) was provided by K. Merritt from a CropMark Direct farm. The fiber was from cotton grown in the 2008-9 cotton season and listed for the FiberMax Certification Program.

Since we had determined that contaminants in fiber can have a significant impact upon the use of fiber DNA for downstream testing we manually cleaned the fibers. This is done by stretching a small amount of fibers (e.g. 1.5 grams) whereby most of the debris is removed with tweezers until no debris can be seen with the naked eye.

DNA extraction was carried out with the Qiagen DNeasy Plant Mini kit with the following steps:

Take 1 gram of cleaned (no leaf trash) mature cotton fiber and put it in a 50 ml Falcon tube. Cut the fibers a few times with clean scissors.

Add 5 ml AP1 lysis buffer (Qiagen cat. 1014630) and 100 µl RNaseA (10 mg/ml). Use a pestle to homogenize the contact between sample and buffer.

Incubate at 65° C. for 20 min, use a 15 ml tube to mix the material 2 to 3 times during the incubation.

Use a 15 ml tube to squeeze the material in order to transfer 500 µl lysate into a 2 ml eppendorf tube. 3 aliquots are taken and used as duplicates.

Add 130 µl AP2 buffer, mix and incubate 5 min on ice to each aliquot.

Centrifuge for 5 min at 13000 rpm.

Transfer the liquid phase to the lilac QIAshredder mini spin column.

Centrifuge for 2 min at 13000 rpm.

Transfer the flow-through to a new eppendorf tube without disturbing the pellet.

Add 800 µl AP3/E buffer and mix.

Transfer 650 µl to the DNeasy mini spin column and centrifuge for 1 min at 8000 rpm, discard the flow-through. Repeat this step with the remaining sample. Discard the collection tube and place the column in a new 2 ml collection tube.

Wash the column with 500 µl AW buffer and centrifuge for 1 min at 8000 rpm, discard the flow-through.

Wash the column with 500 µl AW buffer and centrifuge for 2 min at 13000 rpm, discard the flow-through and collection tube.

Place the column in a 1.5 ml eppendorf tube without ethanol carryover.

Add 50 µl MQ water to the column and incubate at least 5 min at room temperature.

Centrifuge for 1 min at 8000 rpm. Store the DNA at 4° C. (short term) or −20° C. (long term).

Cotyledon DNA extraction of FM9063 B2F was carried out as follows. 50 seeds of FM9063 B2F were germinated with germination paper and water in a 28° C. germinator. Cotyledons were collected and dried with silicon. Cotyledon DNA was extracted. Extracted cotyledon DNA was combined into five 1.5 ml tube.

Whole Genome Amplification was carried out with the Sigma's GenomePlex® Complete Whole Genome Amplification (WGA) Kit (WGA2) with the following steps:

Add 1 µl of 10× Fragmentation Buffer to 10 µl of extracted DNA in a PCR tube.

Incubate in a thermal cycler at 95° C. for 2 minutes and cool on ice.

Add 2 µl of 1× Library Preparation buffer.

Add 1 µl of Library Stabilization Solution and mix.

Incubate in a thermal cycler at 95° C. for 2 minutes and cool on ice.

Add 1 µl of Library Preparation Enzyme and mix.

Incubate in thermal cycler using program WGA1
16° C. for 20 minutes
24° C. for 20 minutes
37° C. for 20 minutes
75° C. for 5 minutes
4° C. forever Add the following master mix:
 7.5 µl 10× Amplification Master Mix
 47.5 µl nuclease-free water
 5 µl WGA polymerase
Incubate in thermal cycler using program WGA2
 95° C. for 3 minutes
 14 cycles of: 94° C. for 15 seconds
  65° C. for 5 minutes
 4° C. forever
Put 5 µl on a 1% agarose gel to check the quality of the WGA DNA. A smear between 100 and 1000 bp should be present.

All the WGA reactions (fiber and cotyledon) proved to be successful.

Optionally the WGA-amplified DNA of cotyledon and fiber of FM9063 B2F was further purified in the following way. Combine WGA DNA from 5 samples into 2 ml tube (about 240 ul DNA), add 24 ul 3M sodium acetate pH5.2 and mix, add 800 ul 100% ice cold ethanol and mix thoroughly and overnight at −20° C., centrifuge at −20° C. for 10 min at 12000 rpm, carefully remove supernatant, wash DNA pellet with 800 ul 70% ice cold ethanol, centrifuge at −20 C for 2 min at 12000 rpm, carefully remove supernatant, put tube in 65° C. incubator for 15 min to dry, resuspend DNA in 65 ul 1×TE buffer.

Two different Taqman assays were carried out on the amplified DNA samples. One Taqman assay aimed at identifying 40 different SNPs and another Taqman assay aimed at identifying 3 different traits: Bollgard II (Mon531), Bollgard (MON15985) and Flex (MON 88913). Each of these Taqman assays were carried out on 4 different samples of DNA: 1) WGA-amplified DNA extracted from FM9063 B2F fiber, 2) WGA-amplified DNA extracted from cotyledon FM9063 B2F, 3) purified WGA-amplified DNA of FM9063 B2F fiber and 4) purified WGA-amplified DNA of FM9063 B2F cotyledon. Because it is known that the cotton A-subgenome (At) is 50% larger that the cotton D-subgenome (Dt) in physical size, 23 SNPs were selected from the A-genome and 17 were selected from the D-genome.

It was observed that all 40 SNPs could be successfully detected in the Taqman assay in purified FM9063 B2F WGA-amplified fiber DNA. In addition, an identical result for the detection of the same 40 SNPs was obtained with the purified FM9063 B2F cotyledon WGA DNA and with raw (i.e. unpurified) FM9063 B2F cotyledon DNA. The Taqman assay for the detection of Bollgard II (Mon531), Bollgard (MON15985), and Flex (MON 88913) also proved to give identical results between the WGA-amplified DNA samples of fiber and cotyledon. Mon531 was assayed according to Yang et al (2005) *J. Agric. Food Chem.* 53, 6222-6229. Mon15985 and Mon88913 were assayed according to Lee et al (2007) *J. Agric. Food Chem.* 55, 3351-3357.

Thus, WGA-amplified cotton fiber DNA can be used as a reliable source for successful molecular marker determination since it provided identical results as a Taqman assay carried out on WGA-amplified leaf DNA. In addition, WGA-amplified cotton fiber DNA can be used as a reliable source for successful trait determination since it provided the same results as a Taqman assay carried out on WGA-amplified leaf DNA.

Although usually a higher number of SNPs (about 300) should be used for the characterization and identification of a specific cotton variety, the present example shows that this approach is feasible by using WGA-amplified cotton fiber DNA.

Example 7

Other Biological Macromolecules Isolated from Cotton Fiber Material

UV spectrophotometry of the extracts using the different protocols for the isolation indicate that these extracts do not consist purely of DNA and may contain other biological macromolecules. Using a Bradford analysis, a low concentration of proteins (about 10 ng/µl) was found. In addition, the fiber extracts contained various concentrations of small RNAs, resistant to RNAse I, which we identified as micro RNAs.

The invention claimed is:

1. A method for identifying a processed cotton fiber comprising the steps of
   a. isolating DNA from said cotton fiber said DNA being naturally occurring in said cotton fiber; and
   b. subjecting said DNA to a detection assay specific for said cotton fiber
   wherein said processed cotton fiber is a cotton fiber which has been subjected to at least one of the process steps selected from the group of ginning, baling, knitting, weaving, scouring, desizing, bleaching, mercerizing, dyeing, waxing, carding, spinning and sizing.

2. The method of claim 1, wherein said detection assay is a polymerase chain reaction based detection assay.

3. The method of claim 1, wherein said detection assay is a nucleic acid hybridization based detection assay.

4. The method of claim 1, wherein said detection assay detects the presence or absence of a chimeric gene present in the genome of the cotton plant producing the fibers.

5. The method of claim 4, wherein said chimeric gene comprises a coding region selected from N-acetylglucosamine transferase, phosphinotricinacetyltransferase, EPSPS, hydroxyphenylpyruvate-dioxygenase, an insecticidal portion of Bacillus thuringiensis crystal protein, poly(ADP-ribose) polymerase, poly(ADP-ribose) glucohydrolase, sucrose synthase, sucrose phosphate synthase, glucanase, cellulose synthase, chitinase, expansin, callose synthase, kinase, nicotinamidase, nicotinate phosphoribosyltransferase, nicotinic acid mononucleotide adenyl transferase, nicotinamide adenine dinucleotide synthetase or nicotine amide phosphorybosyltransferase.

6. The method of claim 4, wherein said detection assay is an event-specific detection assay.

7. The method of claim 1, wherein said detection assay detects the presence or absence of specific alleles present in the genome of the cotton plant producing the fibers.

8. The method of claim 1, wherein said fiber is present in yarns, fabric, or finished apparel.

9. A method for analyzing the genome of a fiber producing cotton plant comprising the steps of
   a. isolating DNA from processed fibers of said cotton plant, said DNA being naturally occurring in said cotton fiber; and
   b. subjecting said DNA to a genome analysis protocol
   wherein said processed cotton fiber is a cotton fiber which has been subjected to at least one of the process steps selected from the group of ginning, baling, knitting, weaving, scouring, desizing, bleaching, mercerizing, dyeing, waxing, carding, spinning and sizing.

10. The method according to claim 9, wherein said isolated DNA is subjected to a whole genome amplification step prior to subjecting said DNA to a genome analysis protocol.

11. The method according to claim 9, wherein said method is applied to yarns, fabrics or finished apparel.

12. A method for isolating naturally occurring DNA from processed cotton fibers comprising the steps of
 a. removing leaf and stem trash material from the cotton fibers; and
 b. incubating said cotton fibers in a lysis buffer containing detergents, proteases and salts for a prolonged time; and
 c. processing said lysis buffer according to standard DNA isolation methods and isolating said naturally occurring DNA
 wherein said processed cotton fiber is a cotton fiber which has been subjected to at least one of the process steps selected from the group of ginning, baling, knitting, weaving, scouring, desizing, bleaching, mercerizing, dyeing, waxing, carding, spinning and sizing.

13. A method for isolating naturally occurring DNA from woven or knitted fabric comprising processed cotton fibers, said method comprising the steps of
a. unweaving the threads of said fabric;
b. incubating said threads in a lysis buffer containing detergents, proteases and salts for a prolonged time; and
c. processing said lysis buffer according to standard DNA isolation methods and isolating said naturally occurring DNA;
wherein said processed cotton fiber is a cotton fiber which has been subjected to at least one of the process steps selected from the group consisting of ginning, baling, knitting, weaving, scouring, desizing, bleaching, mercerizing, dyeing, waxing, carding, spinning and sizing.

14. A method to determine the relative amounts of different cotton fibers in a mixture of processed cotton fibers comprising the steps of
a. isolating from said mixture of cotton fibers DNA naturally occurring in said cotton fibers;
b. subjecting said DNA to detection assays specific for each of said cotton fibers; and
c. determining the relative amount of each of the cotton fibers wherein said processed cotton fiber is a cotton fiber which has been subjected to at least one of the process steps selected from the group consisting of ginning, baling, knitting, weaving, scouring, desizing, bleaching, mercerizing, dyeing, waxing, carding, spinning and sizing.

15. A method to certify the identity of traded cotton fibers, said method comprising:
a. recording purchase of certified cotton seeds by registered growers, said cotton seed comprising a specific genome composition and producing a particular brand of cotton fibers;
b. registering bales of raw cotton fibers produced by said registered growers from said certified cotton seed as said particular brand of cotton fibers;
c. authenticating said bales by cross checking with said seed purchase records;
d. providing said registered bales to mills to produce yarns, fabrics or apparel from said brand of cotton fibers;
e. auditing the identity of said brand of cotton fibers at one or more steps using a method for identifying a processed cotton fiber comprising the steps of
 1. isolating DNA from said cotton fiber, said DNA being naturally occurring in said cotton fiber; and
 2. subjecting said DNA to a detection assay specific for said cotton fiber;
wherein said processed cotton fiber is a cotton fiber which has been subjected to at least one of the process steps selected from the group of ginning, baling, knitting, weaving, scouring, desizing, bleaching, mercerizing, dyeing, waxing, carding, spinning and sizing.

16. The method of claim 12, wherein said prolonged time is a period of 4 to 100 hours.

17. The method of claim 13, wherein said prolonged time is a period of 4 to 100 hours.

18. The method of claim 15, wherein said registered bales are provided to mills to produce yarns, fabrics or apparel predominantly from said brand of cotton fibers.

19. The method of claim 15, wherein said registered bales are provided to mills to produce yarns, fabrics or apparel exclusively from said brand of cotton fibers.

\* \* \* \* \*

SEQUENCE LISTING

<160> NUMBER OF SEQ ID NOS: 18

<210> SEQ ID NO 1
<211> LENGTH: 23
<212> TYPE: DNA
<213> ORGANISM: Artificial
<220> FEATURE:
<223> OTHER INFORMATION: oligonucleotide 1 for PCR amplification of
      Ghgluc1

<400> SEQUENCE: 1
ggccgaagcc gatcttatct agg                                           23

<210> SEQ ID NO 2
<211> LENGTH: 23
<212> TYPE: DNA
<213> ORGANISM: Artificial
<220> FEATURE:
<223> OTHER INFORMATION: oligonucleotide 2 for PCR amplification of
      Ghgluc1

<400> SEQUENCE: 2
cggcaacaat cttccatctc cag                                           23

```
<210> SEQ ID NO 3
<211> LENGTH: 55
<212> TYPE: DNA
<213> ORGANISM: Artificial
<220> FEATURE:
<223> OTHER INFORMATION: oligonucleotide 1 for PCR amplification of NodC

<400> SEQUENCE: 3
cgtttttcac tcatcgtcgt tttcaagtgt cgtagatgtg atcggtttgc ttgcg        55

<210> SEQ ID NO 4
<211> LENGTH: 33
<212> TYPE: DNA
<213> ORGANISM: Artificial
<220> FEATURE:
<223> OTHER INFORMATION: oligonucleotide 2 for PCR amplification of NodC

<400> SEQUENCE: 4
ggcgcgcctt aggaactctc gcgtgatagc cac                                33

<210> SEQ ID NO 5
<211> LENGTH: 23
<212> TYPE: DNA
<213> ORGANISM: Artificial
<220> FEATURE:
<223> OTHER INFORMATION: oligonucleotide 1 for PCR amplification of
      expansin

<400> SEQUENCE: 5
gggagcttgt ggttatggaa acc                                           23

<210> SEQ ID NO 6
<211> LENGTH: 25
<212> TYPE: DNA
<213> ORGANISM: Artificial
<220> FEATURE:
<223> OTHER INFORMATION: oligonucleotide 2 for PCR amplification of
      expansin

<400> SEQUENCE: 6
cagggacgat cccagctcga tattc                                         25

<210> SEQ ID NO 7
<211> LENGTH: 25
<212> TYPE: DNA
<213> ORGANISM: Artificial
<220> FEATURE:
<223> OTHER INFORMATION: oligonucleotide 1 for Taqman detection assay of
      GhGluc1 (forward primer)

<400> SEQUENCE: 7
gcttttggaa gcgatataac atcga                                         25

<210> SEQ ID NO 8
<211> LENGTH: 25
<212> TYPE: DNA
<213> ORGANISM: Artificial
<220> FEATURE:
<223> OTHER INFORMATION: oligonucleotide 2 for Taqman detection assay of
      GhGluc1 (reverse primer)

<400> SEQUENCE: 8
ggcataggca aaataagggt acaca                                         25

<210> SEQ ID NO 9
<211> LENGTH: 16
<212> TYPE: DNA
```

```
<213> ORGANISM: Artificial
<220> FEATURE:
<223> OTHER INFORMATION: oligonucleotide 3 for Taqman detection assay of
      GhGluc1 (VIC marked oligonucleotide detecting the G. hirsitum
      allele of Gluc1)

<400> SEQUENCE: 9
aatcctgtcg aaccag                                                        16

<210> SEQ ID NO 10
<211> LENGTH: 15
<212> TYPE: DNA
<213> ORGANISM: Artificial
<220> FEATURE:
<223> OTHER INFORMATION: oligonucleotide 4 for Taqman detection assay of
      GhGluc1 (FAM marked oligonucleotide detecting the G. barbadense
      allele of Gluc1)

<400> SEQUENCE: 10
atcctgtcaa accag                                                         15

<210> SEQ ID NO 11
<211> LENGTH: 24
<212> TYPE: DNA
<213> ORGANISM: artificial
<220> FEATURE:
<223> OTHER INFORMATION: oligonucleotide 1 for PCR amplification of
      rpl16

<400> SEQUENCE: 11
gctatgctta gtgtgtgact cgtt                                               24

<210> SEQ ID NO 12
<211> LENGTH: 23
<212> TYPE: DNA
<213> ORGANISM: artificial
<220> FEATURE:
<223> OTHER INFORMATION: oligonucleotide 2 for PCR amplification of
      rpl16

<400> SEQUENCE: 12
cccttcattc ttcctctatg ttg                                                23

<210> SEQ ID NO 13
<211> LENGTH: 24
<212> TYPE: DNA
<213> ORGANISM: artificial
<220> FEATURE:
<223> OTHER INFORMATION: oligonucleotide 1 for PCR amplification of matK

<400> SEQUENCE: 13
ctaatggatc aacagaawcg tttg                                               24

<210> SEQ ID NO 14
<211> LENGTH: 19
<212> TYPE: DNA
<213> ORGANISM: artificial
<220> FEATURE:
<223> OTHER INFORMATION: oligonucleotide 2 for PCR amplification of matK

<400> SEQUENCE: 14
aactagtcgg atggagtag                                                     19

<210> SEQ ID NO 15
<211> LENGTH: 30
<212> TYPE: DNA
<213> ORGANISM: artificial
```

-continued

```
<220> FEATURE:
<223> OTHER INFORMATION: oligonucleotide 1 for PCR amplification of
      trnT- trnL

<400> SEQUENCE: 15
aatattactg actccmtttt kattttckag                              30

<210> SEQ ID NO 16
<211> LENGTH: 20
<212> TYPE: DNA
<213> ORGANISM: artificial
<220> FEATURE:
<223> OTHER INFORMATION: oligonucleotide 2 for PCR amplification of
      trnT- trnL

<400> SEQUENCE: 16
tctaccgatt tcgccatatc                                         20

<210> SEQ ID NO 17
<211> LENGTH: 20
<212> TYPE: DNA
<213> ORGANISM: artificial
<220> FEATURE:
<223> OTHER INFORMATION: oligonucleotide 1 for PCR amplification of ndhF

<400> SEQUENCE: 17
gaatatgcat ggatcatacc                                         20

<210> SEQ ID NO 18
<211> LENGTH: 26
<212> TYPE: DNA
<213> ORGANISM: artificial
<220> FEATURE:
<223> OTHER INFORMATION: oligonucleotide 2 for PCR amplification of ndhF

<400> SEQUENCE: 18
cgaaacatat aaaatgcrgt taatcc                                  26
```